United States Patent
Surmeier, Jr. et al.

(10) Patent No.: US 11,554,103 B2
(45) Date of Patent: Jan. 17, 2023

(54) COMPOSITIONS AND METHODS TO REDUCE PHARMACEUTICAL-INDUCED TOXICITY

(71) Applicant: Northwestern University, Evanston, IL (US)

(72) Inventors: Dalton James Surmeier, Jr., Chicago, IL (US); Steven M. Graves, Chicago, IL (US)

(73) Assignee: Northwestern University, Evanston, IL (US)

( * ) Notice: Subject to any disclaimer, the term of this patent is extended or adjusted under 35 U.S.C. 154(b) by 367 days.

Patent file contains an affidavit/declaration under 37 CFR 1.130(b).

(21) Appl. No.: 15/809,079

(22) Filed: Nov. 10, 2017

(65) Prior Publication Data
US 2018/0153839 A1 Jun. 7, 2018

Related U.S. Application Data

(60) Provisional application No. 62/420,369, filed on Nov. 10, 2016.

(51) Int. Cl.
| | | |
|---|---|---|
| A61K 31/198 | (2006.01) | |
| A61K 31/395 | (2006.01) | |
| A61P 25/16 | (2006.01) | |
| A61K 31/137 | (2006.01) | |

(52) U.S. Cl.
CPC .......... *A61K 31/198* (2013.01); *A61K 31/395* (2013.01); *A61P 25/16* (2018.01); *A61K 31/137* (2013.01); *C12Y 104/03004* (2013.01)

(58) Field of Classification Search
CPC .................................................. A61K 31/198
See application file for complete search history.

(56) References Cited

U.S. PATENT DOCUMENTS

| | | | |
|---|---|---|---|
| 4,657,760 A | 4/1987 | Kung | |
| 5,206,344 A | 4/1993 | Katre et al. | |
| 5,225,212 A | 7/1993 | Martin et al. | |
| 2006/0100136 A1* | 5/2006 | Kirk | A61K 31/137 514/211.1 |
| 2010/0286124 A1* | 11/2010 | Gant | A61K 31/4985 514/217.02 |

FOREIGN PATENT DOCUMENTS

| | | |
|---|---|---|
| WO | WO 2004097009 | 11/2004 |
| WO | WO 2005075465 | 8/2005 |

OTHER PUBLICATIONS

Brand, Mitochondrial generation of superoxide and hydrogen peroxide as the source of mitochondrial redox signaling. Free Radic Biol Med. 2016; 100:14-31.

Brichta et al., Identification of neurodegenerative factors using translatome-regulatory network analysis, Nat Neurosci, vol. 18(9), pp. 1325-1333, 2015.
Callaghan et al., Incidence of Parkinson's disease among hospital patients with methamphetamine-use disorders. Mov Disord, 2010; 25(14):2333-2339.
Callaghan et al., Increased risk of Parkinson's disease in individuals hospitalized with conditions related to the use of methamphetamine or other amphetamine-type drugs, Drug Alcohol Depend, vol. 120, pp. 35-40, 2012.
Chen et al., A Spontaneous Point Mutation Produces Monoamine Oxidase A/B Knock-out Mice with Greatly Elevated Monoamines and Anxiety-like Behavior, J Biol Chem, vol. 279(38), pp. 39645-39652, 2004.
Christine et al., Development of Parkinson's disease in patients with Narcolepsy. J Neural Transm. 2012; 119(6):697-699.
Cooper et al., Familial Parkinson's disease iPSCs show cellular deficits in mitochondrial responses that can be pharmacologically rescued, Sci Transl Med, vol. 4(141), pp. 141ra190, 2012.
Curtin et al., Methamphetamine/amphetamine abuse and risk of Parkinson's disease in Utah: a population-based assessment, Drug Alcohol Depend, vol. 146, pp. 30-38, 2016.
Day et al., Selective elimination of glutamatergic synapses on striatopallidal neurons in Parkinson disease models, Nat Neurosci, vol. 9, pp. 251-259, 2006.
Dryanovski et al., Calcium Entry and α-Synuclein Inclusions Elevate Dendritic Mitochondrial Oxidant Stress in Dopaminergic Neurons, J Neurosci, vol. 33(24), pp. 10154-10164, 2013.
Fahn et al., The oxidant stress hypothesis in Parkinson's disease: evidence supporting it. Ann Neurol. 1992; 32:904-812.
Guzman et al., Oxidant stress evoked by pacemaking in dopaminergic neurons is attenuated by DJ-1, Nature, vol. 468(7324), pp. 696-700, 2010.
Heiman et al., Cell-Type-Specific mRNA Purification by Translating Ribosome Affinity Purification (TRAP), Nat Protoc, vol. 9(6), pp. 1282-1291, 2014.
Hille, B., Ion channels of excitable embranes. 3rd edn, (Sinauer, 2001).
Hodgkins et al., The Pharmacology and Clinical Outcomes of Amphetamines to Treat ADHD: Does Composition Matter?, CNS Drugs, vol. 26(3), pp. 245-268, 2012.
Ilijic et al., The L-type channel antagonist isradipine is neuroprotective in a mouse model of Parkinson's disease, Neurobiol Dis, vol. 43(2), pp. 364-371, 2011.
Kaludercic et al., Reactive oxygen species and redox compartmentalization, Front Physiol, vol. 5, article 285, 2014.
Kriks et al., Floor plate-derived dopamine neurons from hESCs efficiently engraft in animal models of PD, vol. 480(7378), pp. 547-551, 2011.
Lamensdorf et al., Effect of Long-Term Treatment with Selective Monoamine Oxidase A and B Inhibitors on Dopamine Release from Rat Striatum In Vivo. J Neurochem. 1996; 67:1532-1539.

(Continued)

*Primary Examiner* — Yong S. Chong
(74) *Attorney, Agent, or Firm* — Casimir Jones SC; David W. Staple

(57) ABSTRACT

Provided herein are compositions and methods to reduce toxicity resulting from pharmaceutical treatment, that can lead to increased risk of developing Parkinson's disease (PD) and/or acceleration of PD-associated deterioration.

9 Claims, 17 Drawing Sheets

(56) References Cited

OTHER PUBLICATIONS

Mazzulli et al., Gaucher Disease Glucocerebrosidase and α-Synuclein Form a Bidirectional Pathogenic Loop in Synucleinopathies, Cell, vol. 146(1), pp. 37-52, 2011.

Mohsarov et al., Interplay between Cytosolic Dopamine, Calcium, and α-Synuclein Causes Selective Death of Substantia Nigra Neurons, Neuron, vol. 62(2), pp. 218-229, 2009.

Pacelli et al., Elevated Mitochondrial Bioenergetics and Axonal Arborization Size Are Key Contributors to the Vulnerability of Dopamine Neurons, Curr Biol, vol. 25(18), pp. 2349-2360, 2015.

Pifl et al., Mechanism of the dopamine-releasing actions of amphetamine and cocaine: plasmalemmal dopamine transporter versus vesicular monoamine transporter. Mol Pharmacol. 1995; 47(2):368-373.

Sabharwal et al., Peroxiredoxin-5 targeted to the mitochondrial intermembrane space attenuates hypoxia-induced reactive oxygen species signalling, Biochem J, vol. 456(3), 337-346, 2013.

Sawhney et al., Bioerodible hydrogels based on photopolymerized poly(ethylene glycol)-co-poly(.alpha.-hydroxy acid) diacrylate macromers. Macromolecules. 1993; 26(4):581-587.

Segura-Aguilar et al., Protective and toxic roles of dopamine in Parkinson's disease, J Neurochem, vol. 129(6), pp. 898-915, 2014.

Seibler et al., Mitochondrial Parkin Recruitment Is Impaired in Neurons Derived from Mutant PINK1 Induced Pluripotent Stem Cells, J Neurosci, vol. 31(16), pp. 5970-5976, 2011.

Sulzer et al., Mechanisms of neurotransmitter release by amphetamines: A review. Prog Neurobiol. 2005; 75(6):406-433.

Surmeier et al., Calcium, bioenergetics and neuronal vulnerability in Parkinsons disease, J Biol Chem, vol. 288, pp. 10736-10741, 2013.

West et al., Unbiased stereological estimation of the total number of neurons in the subdivisions of the rat hippocampus using the optical fractionator. Anat Rec. 1991; 231(4):482-497.

Woodard et al., iPSC-Derived Dopamine Neurons Reveal Differences between Monozygotic Twins Discordant for Parkinson's Disease, Cell Reports, vol. 9(4), pp. 1173-1182, 2014.

\* cited by examiner a *Axonal mitochondrial oxidant stress* b *Dendritic mitochondrial oxidant stress*

COMPOSITIONS AND METHODS TO REDUCE PHARMACEUTICAL-INDUCED TOXICITY

CROSS-REFERENCE TO RELATED APPLICATIONS

The present invention claims priority to U.S. Provisional Patent Application 62/420,369, filed Nov. 10, 2016, which is incorporated by reference in its entirety.

STATEMENT REGARDING FEDERAL FUNDING

This invention was made with government support under P50 NS047085 and K99 DA039253 awarded by the National Institutes of Health. The government has certain rights in the invention.

FIELD

Provided herein are compositions and methods to reduce toxicity resulting from pharmaceutical treatment, that can lead to increased risk of developing Parkinson's disease (PD) and/or acceleration of PD-associated deterioration.

BACKGROUND

Methamphetamine (Desoxyn) and amphetamine (Adderall) are potent psychostimulants that are FDA-approved to treat attention deficit hyperactivity disorder (ADHD) and obesity (amphetamine is also approved to treat narcolepsy). Clinical evidence has now emerged indicating that methamphetamine/amphetamine use increases the risk of developing Parkinson's disease (PD). PD is the most common neurodegenerative movement disorder and there is currently no available therapy to prevent disease progression. Levodopa (L-DOPA) treatment is a mainstay for early and mid-stage PD patients. Although it is initially effective in alleviating symptoms, as the disease progresses, L-DOPA becomes less effective and the dose required to achieve symptomatic benefit rises. In most patients, high doses of L-DOPA produce unwanted dyskinetic movements. Alternative therapeutic strategies that reduce the likelihood of inducing development of PD and/or reduce the degenerative side effects of L-DOPA treatment are needed.

SUMMARY

Provided herein are compositions and methods to reduce toxicity resulting from pharmaceutical treatment, that can lead to increased risk of developing Parkinson's disease (PD) and/or acceleration of PD-associated deterioration.

In some embodiments, provided herein are methods of reducing mitochondrial stress in a cell comprising delivering monoamine oxidase (MAO) inhibitor and/or Cav1 inhibitor to the cell. In some embodiments, the monoamine oxidase inhibitor is a nonselective MAO-A/MAO-B inhibitor. In some embodiments, the nonselective MAO-A/MAO-B inhibitor is selected from the group consisting of isocarboxazid, nialamide, phenelzine, hydracarbazine, and tranylcypromine. In some embodiments, the monoamine oxidase inhibitor is an MAO-A inhibitor. In some embodiments, the MAO-A inhibitor is selected from the group consisting of bifemelane, moclobemide, pirlindole, toloxatone. In some embodiments, the monoamine oxidase inhibitor is an MAO-B inhibitor. In some embodiments, the MAO-A inhibitor is selected from the group consisting of selegiline and rasagiline. In some embodiments, the cell is within a subject and the MAO inhibitor and/or Cav1 inhibitor are administered to the subject. In some embodiments, the subject has also been administered amphetamine, methamphetamine, and/or levodopa. In some embodiments, the subject has also been administered amphetamine for the treatment of attention deficit hyperactive disorder (ADHD), narcolepsy, or obesity. In some embodiments, the subject has also been administered methamphetamine for the treatment of attention deficit hyperactive disorder (ADHD), narcolepsy, or obesity. In some embodiments, the subject has also been administered levodopa for the treatment of Parkinson's disease.

In some embodiments, provided herein are methods of treating attention deficit hyperactive disorder (ADHD) comprising administering to the subject: (a) a therapeutic agent useful in the treatment or reduction of symptoms associated with ADHD, and (b) (i) a mitochondrial stress reduction agent and/or (ii) a neurodegeneration protective agent. In some embodiments, the therapeutic agent and the (i) mitochondrial stress reduction agent and/or (ii) neurodegeneration protective agent are in a single pharmaceutical composition. In some embodiments, the therapeutic agent and the (i) mitochondrial stress reduction agent and/or (ii) neurodegeneration protective agent are in separate pharmaceutical compositions. In some embodiments, the separate pharmaceutical compositions are administered concurrently. In some embodiments, the separate pharmaceutical compositions are administered separately. In some embodiments, the therapeutic agent comprises amphetamine or methamphetamine. In some embodiments, the (i) mitochondrial stress reduction agent and/or (ii) neurodegeneration protective agent comprises a monoamine oxidase inhibitor and/or a Cav1 inhibitor. In some embodiments, the monoamine oxidase inhibitor is rasagiline. In some embodiments, the Cav1 inhibitor is a dihydropyridine (e.g. isradipine).

In some embodiments, provided herein are methods of treating Parkinson's disease comprising (a) administering to the subject: (a) a therapeutic agent useful in the treatment or reduction of symptoms associated with Parkinson's disease, and (b) (i) a mitochondrial stress reduction agent and/or (ii) a neurodegeneration protective agent. In some embodiments, the therapeutic agent and the (i) mitochondrial stress reduction agent and/or (ii) neurodegeneration protective agent are in a single pharmaceutical composition. In some embodiments, the therapeutic agent and the (i) mitochondrial stress reduction agent and/or (ii) neurodegeneration protective agent are in separate pharmaceutical compositions. In some embodiments, the separate pharmaceutical compositions are administered concurrently. In some embodiments, the separate pharmaceutical compositions are administered separately. In some embodiments, the therapeutic agent comprises levodopa. In some embodiments, the (i) mitochondrial stress reduction agent and/or (ii) neurodegeneration protective agent comprises a monoamine oxidase inhibitor and/or a Cav1 inhibitor. In some embodiments, the monoamine oxidase inhibitor is rasagiline. In some embodiments, the Cav1 inhibitor is a dihydropyridine.

In some embodiments, provided herein are pharmaceutical compositions comprising (a) a therapeutic agent selected from amphetamine, methamphetamine, and levodopa; and (b) (i) a mitochondrial stress reduction agent and/or (ii) a neurodegeneration protective agent selected from a monoamine oxidase (MAO) inhibitor and/or (Cav1) Cav1 inhibitor. In some embodiments, the monoamine oxidase inhibitor is a nonselective MAO-A/MAO-B inhibitor. In some embodiments, the nonselective MAO-A/MAO-B inhibitor is selected from the group consisting of isocarboxazid, nialamide, phenelzine, hydracarbazine, and tranylcypromine. In some embodiments, the monoamine oxidase inhibitor is an MAO-A inhibitor. In some embodiments, the MAO-A inhibitor is selected from the group consisting of bifemelane, moclobemide, pirlindole, toloxatone. In some embodiments, the monoamine oxidase inhibitor is an MAO-B inhibitor. In some embodiments, the MAO-A inhibitor is selected from the group consisting of selegiline and rasagiline.

In some embodiments, provided herein is the use of the pharmaceutical compositions described herein for the treatment of attention deficit hyperactive disorder (ADHD), narcolepsy, obesity, or Parkinson's disease.

In some embodiments, provided herein are kits or systems comprising (a) a first pharmaceutical composition comprising a therapeutic agent selected from amphetamine, methamphetamine, and levodopa; and (b) a second pharmaceutical composition comprising (i) a mitochondrial stress reduction agent and/or (ii) a neurodegeneration protective agent, selected from a monoamine oxidase (MAO) inhibitor and/or Cav1 inhibitor. In some embodiments, the monoamine oxidase inhibitor is a nonselective MAO-A/MAO-B inhibitor. In some embodiments, the nonselective MAO-A/MAO-B inhibitor is selected from the group consisting of isocarboxazid, nialamide, phenelzine, hydracarbazine, and tranylcypromine, in some embodiments, the monoamine oxidase inhibitor is an MAO-A inhibitor. In some embodiments, the MAO-A inhibitor is selected from the group consisting of bifemelane, moclobemide, pirlindole, toloxatone. In some embodiments, the monoamine oxidase inhibitor is an MAO-B inhibitor. In some embodiments, the MAO-A inhibitor is selected from the group consisting of selegiline and rasagiline.

In some embodiments, provided herein is the use of the kits or systems described herein for the treatment of attention deficit hyperactive disorder (ADHD), narcolepsy, obesity, or Parkinson's disease.

+l-dopa increased axonal mitochondrial stress in the intermembrane space compared to control (middle; n=9 axons; Wilcoxon matched-pairs signed rank test; p=0.0039). +l-dopa-induced stress was prevented by MAO inhibition with 5 μM clorgyline +10 μM rasagiline (right; MAOi; n=9 axons; Wilcoxon matched-pairs signed rank test; p=0.25). (Panel E) Mitochondrial membrane potential was measured with TMRM to demonstrate the transfer of electrons to mitochondria by MAO metabolism of DA; sample one photon image of an iPSC loaded with TMRM dye (upper left) and high magnification image highlighting an axonal segment (lower right); scale bars denote 10 μm. (Panel F) Addition of 1 μM myxothiazol to inhibit complex III and 1 μM carboxyatractyloside to inhibit adenine nucleotide translocase resulted in fluorescent decay of the TMRM signal. This decay was fit mathematically with a polynomial to establish baseline decay (FIG. S8). The observed data was normalized to the decay fit, generating a polarization index, with deviations from 1.0 indicating deviation from the fitting equation. Perfusion of 100 levodopa (+l-dopa; n=18 axons) caused a significant deviation and was prevented by MAOi (n=15 axons); data presented as median ±interquartile range. *p<0.05.

Figure 7:
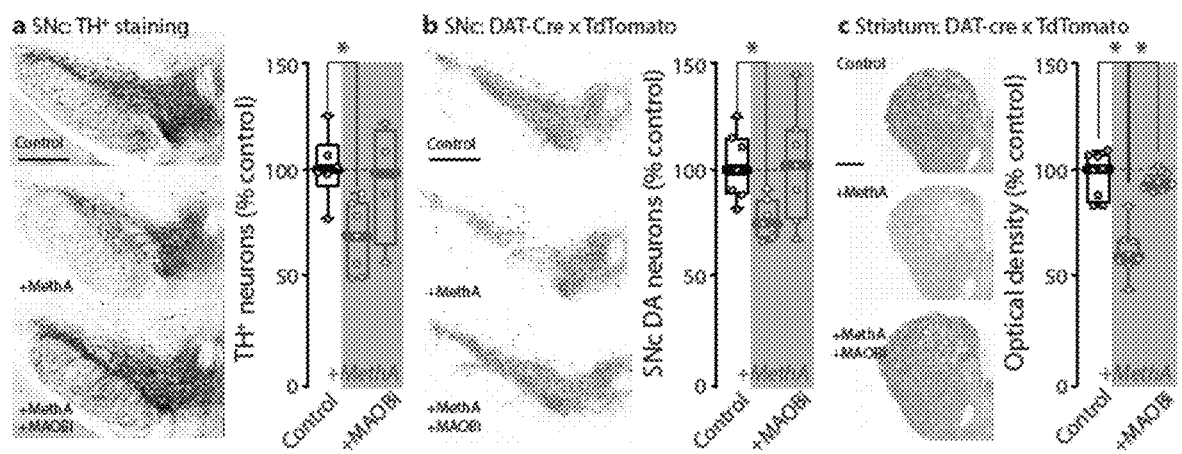

FIG. 7. Chronic in vivo methamphetamine administration was neurotoxic. (Panel A) Sample images depicting methamphetamine (+methA; 5 mg/kg)-induced loss of tyrosine hydroxylase expressing neurons (left) in the substantia nigra pars compacta (SNc) which was prevented by monoamine oxidase inhibition (1 mg/kg rasagiline pretreatment; +MAOBi). Stereological quantification indicates a loss of tyrosine hydroxylase expressing neurons (TH$^+$ neurons) after +methA that was prevented with +MAOBi (right); control n=6, +methA n=7, and +MAOBi n=4 mice; Kruskal-Wallis test; p=0.0291). (Panel B) Sample images depicting methamphetamine (+methA; 5 mg/kg)-induced loss of labeled neurons from Dat-Cre X Ai14 mice (left) which was prevented by monoamine oxidase inhibition (1 mg/kg rasagiline 30 min pretreatment; MAOBi). Stereological quantification indicates a loss of SNc neurons after +methA that was prevented with +MAOBi (right); control n=7, +methA n=7, and +MAOBi n=7 mice (Kruskal-Wallis test; p=0.0267). (Panel C) +methA also led to a loss of SNc axons in the striatum which was prevented by +MAOBi (left), changes quantified by optical density measurements (right); control n=8, +methA n=8, and +MAOBi n=8 mice (Kruskal-Wallis test; p=0.0005). Scale bars denote 500 μm; *p<0.05.

Figure 8:
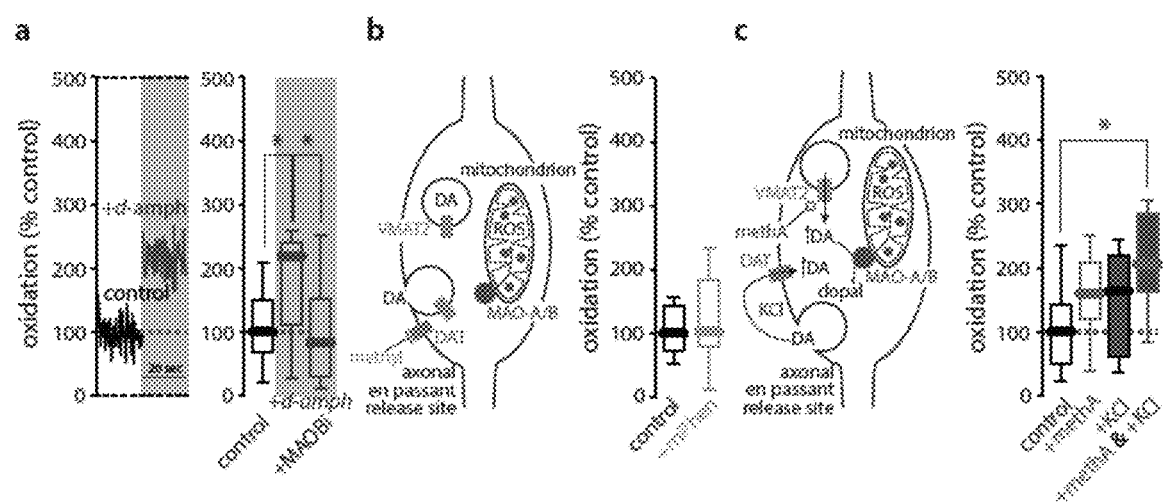

FIG. 8. Amphetamine but not methylphenidate increased mitochondrial stress and subthreshold methamphetamine paired with electrical activity was sufficient to induce stress. (Panel A) Sample traces depicting the effects of 10 μM d-amphetamine (+d-amph), on axonal mitochondrial stress. +d-amph (n=13 slices/4 mice) increased axonal mitochondrial stress compared to control (n=13 slices/5 mice) and was prevented by 10 μM rasagiline (+MAOBi; n=13 slices/3 mice); Kruskal-Wallis test; p=0.0025. (Panel B) Cartoon (left) depicting actions of methylphenidate (+mPhen; 5 μM). +mPhen had no effect (right) on axonal mitochondrial stress (n=11 slices/3 mice); Wilcoxon matched-pairs signed rank test; p=0.4131. (Panel C) Cartoon (left) depicting convergence of 1 μM methamphetamine (+methA) and electrical activity (induced by 15 mM KCl) on cytosolic dopamine and mitochondria. Axonal mitochondrial stress was not significantly altered (right) by 1 μM +methA (n=17 slices/6 mice) or 15 mM KCl (+KCl; n=12 slices/3 mice) relative to control (n=13 slice/3 mice) but was increased by the combination of +methA and +KCl (n=14 slices/5 mice); Kruskal-Wallis test; p=0.0047. *p<0.05.

Figure 9:
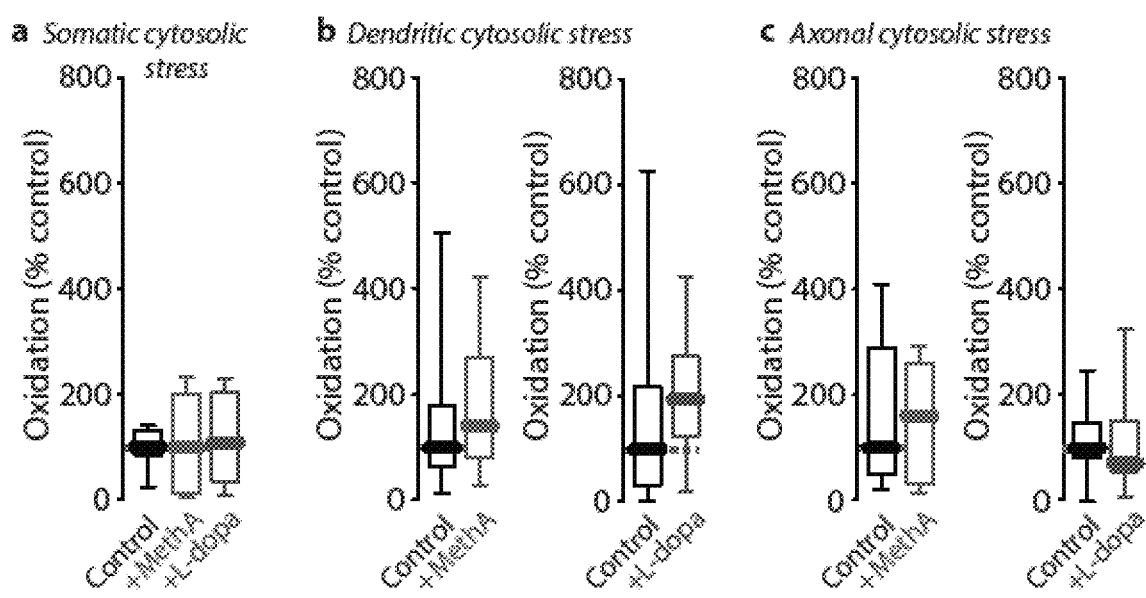

FIG. 9. Methamphetamine and levodopa had no effect on cytosolic stress. The redox sensitive probe roGFP was targeted to the cytosolic compartment of substantia nigra pars compacta dopaminergic neurons and levels of oxidant stress measured. (Panel A) Somatic cytosolic stress was unaltered by 10 μM methamphetamine (+methA; n=10 cells/3 mice) or 100 μM levodopa (+l-dopa; n=11 cells/3 mice); control n=11 cells/2 mice; Kruskal-Wallis test; p=0.9154. (Panel B) Neither +methA (left; n=10 slices/5 mice; Mann Whitney test; p=0.6606) or +l-dopa (right; n=10 slices/4 mice; Mann Whitney test; p=0.3562) altered cytosolic stress in distal dendrites (+methA control n=14 slices/4 mice; +l-dopa control n=9 slices/3 mice). (Panel C) Similar to dendrites, neither +methA (left; n=11 slices/4 mice) or +l-dopa (right; n=13 slices/4 mice) altered axonal cytosolic stress; +methA ctrl n=11 slices/3 mice (Mann Whitney test; p=0.9476); +l-dopa ctrl n=10 slices/3 mice (Mann Whitney test; p=0.5558).

Figure 10:
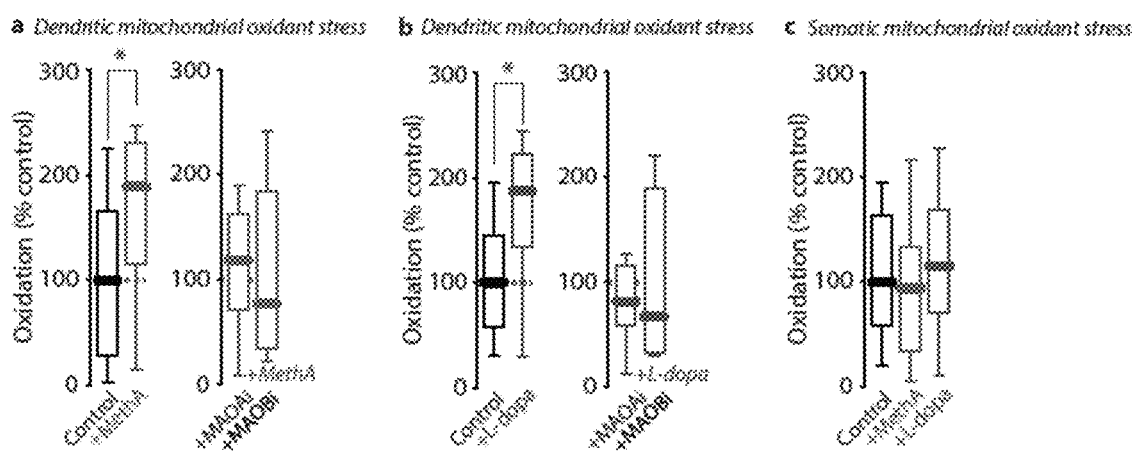

FIG. 10. Dendritic mitochondrial stress was increased by methamphetamine and levodopa in a monamine oxidase-dependent manner but somatic stress was unaltered. The redox sensitive probe roGFP was targeted to the mitochondrial matrix of substantia nigra pars compacta dopaminergic neurons and levels of oxidant stress measured. (Panel A) Dendritic mitochondrial stress was increased by 10 μM methamphetamine (+methA; left) and was prevented (right) by 5 μM clorgyline (+MAOAi) or 10 μM rasagiline (+MAOBi); control n=14 slices/6 mice; +methA n=19 slices/8 mice; +MAOAi n=13 slices/5 mice; +MAOBi n=12 slices/4 mice (Kruskal-Wallis test; p=0.0241). (Panel B) Dendritic mitochondrial stress was increased by 100 μM levodopa (+l-dopa; left) and was prevented (right) by 5 μM clorgyline (+MAOAi) or 10 μM rasagiline (+MAOBi); control n=19 slices/6 mice; +l-dopa n=16 slices/6 mice; +MAOAi n=9 slices/3 mice; +MAOBi n=11 slices/4 mice; Kruskal-Wallis test; p=0.0034. (Panel C) Somatic mitochondrial stress was unchanged by treatments; control (n=11 cells/6 mice), 10 μM methamphetamine (+methA; n=12 cells/4 mice), or 100 μM levodopa (+l-dopa; n=18 cells/5 mice); Kruskal-Wallis test; p=0.5341. *p<0.05.

Figure 11:
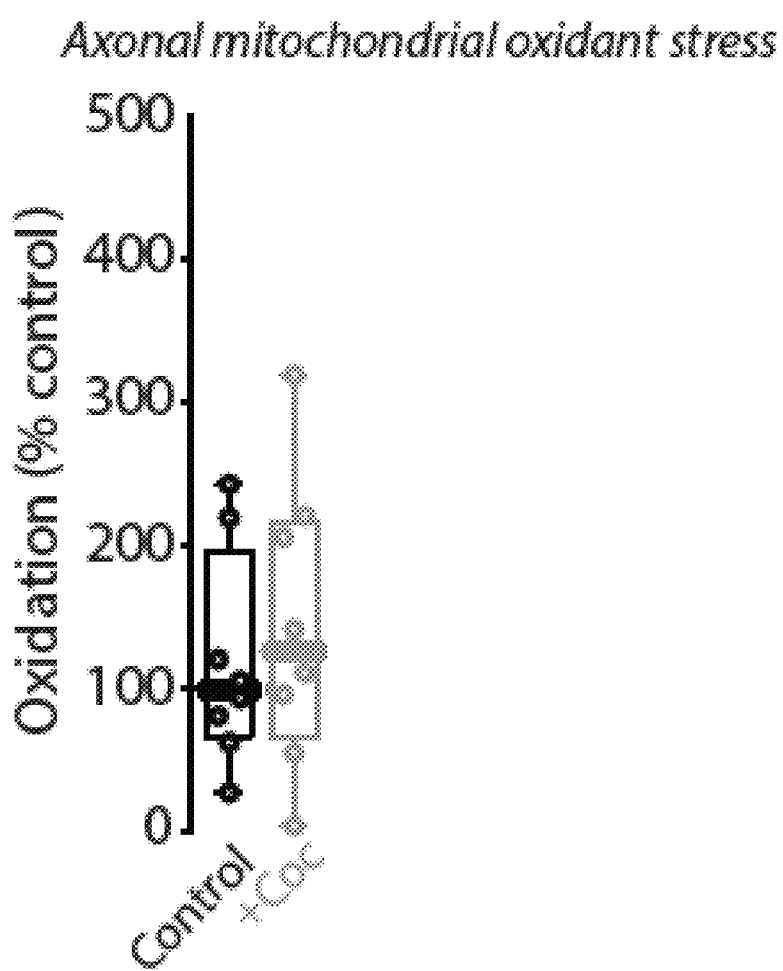

FIG. 11. Cocaine had no effect on mitochondrial stress. Ex vivo slices were prepared from mice expressing the redox sensitive probe roGFP targeting the mitochondrial matrix. Cocaine (5 μM; +coc) had no effect on mitochondrial stress in substantia nigra pars compacta dopaminergic axons (Mann Whitney test pj=0.6454; n=8 slices/2 mice; *p<0.05.

Figure 1:
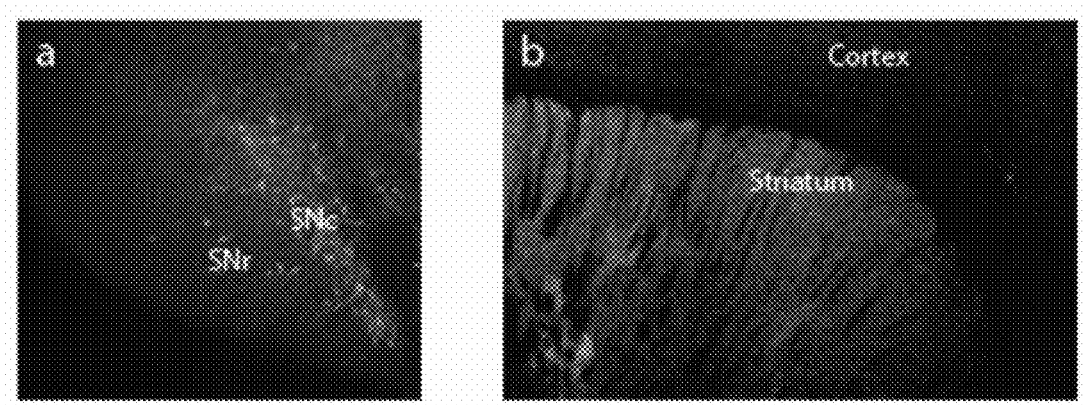
FIG. 1. TH-GFP fluorescence. Sample images depicting expression patter of green fluorescent protein expressed under the tyrosine hydroxylase promoter in the compacta (SNc), reticulata (SNr; Panel a) and dorsolateral striatum (Panel b).
Figure 12:
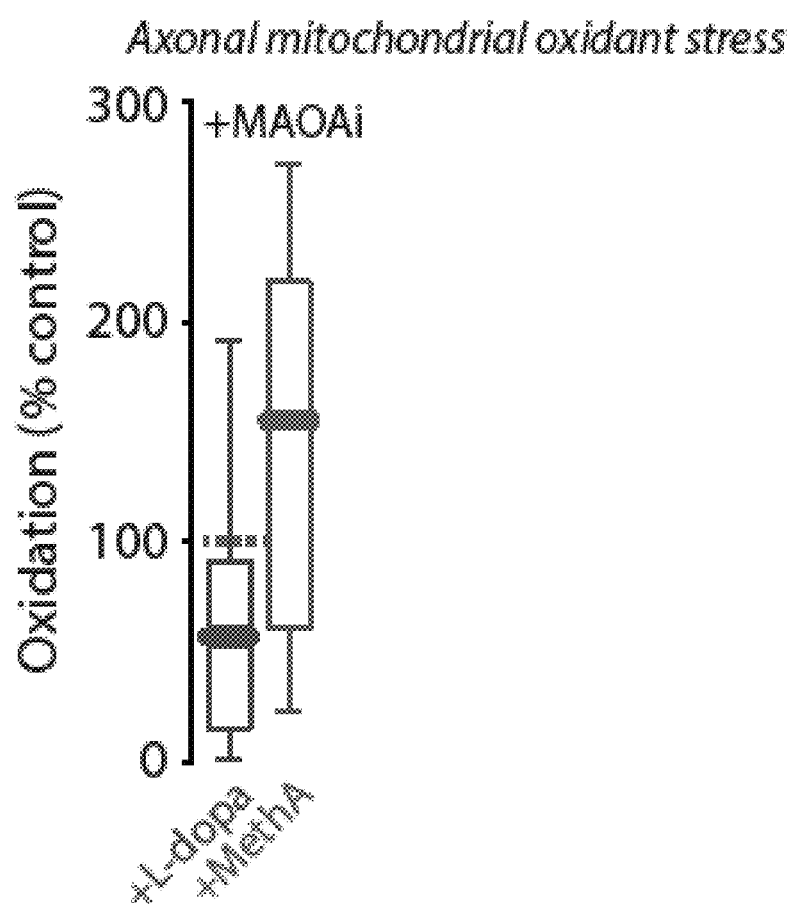

FIG. 12. Monoamine oxidase A inhibition attenuated methamphetamine and levodopa-induced axonal mitochondrial stress. The redox sensitive probe roGFP was targeted to the mitochondrial matrix of substantia nigra pars compacta dopaminergic neurons and the ability of clorgyline (5 μM; +MAOAi), a monoamine oxidase A inhibitor, to prevent 100 μM levodopa (+l-dopa; n=12 slices/3 mice; analyzed with FIG. 1D) or 10 μM methamphetamine (+methA; n=12 slices/4 mice; analyzed with FIG. 1A) induced axonal stress determined. Monoamine oxidase A inhibition prevented rises in mitochondrial stress.

Figure 13:
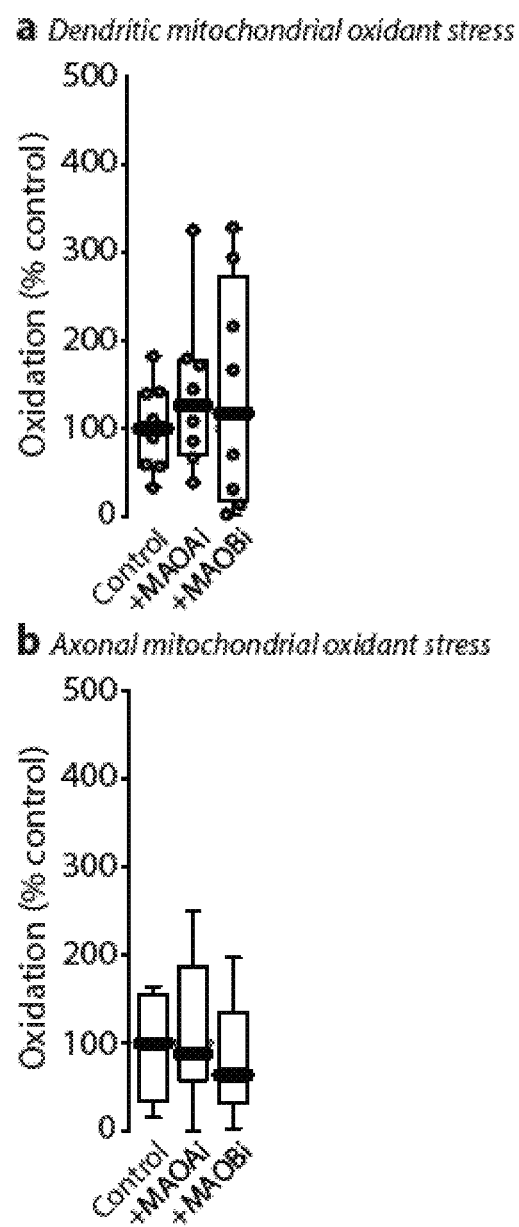

FIG. 13. Monoamine oxidase inhibition alone had no effect on mitochondrial stress. Ex vivo slices were prepared from mice expressing the redox sensitive probe in the mitochondrial matrix and redox status assessed with aCSF (control), 5 μM clorgyline (+MAOAi; monoamine oxidase A inhibitor), or 10 μM rasagiline (+MAOBi; monoamine oxidase B inhibitor) in dendrites (Panel A) and axons (Panel B). Monoamine oxidase inhibitors had no effect on mitochondrial stress; dendrite control n=8 slices/3 mice, dendrite +MAOAi n=8 slices/3 mice, dendrite +MAOBi n=8 slices/3 mice (Kruskal-Wallis test; p=0.7577); axonal control n=10 slices/3 mice, axonal +MAOAi n=11 slices/3 mice, axonal +MAOBi n=11 slices/3 mice (Kruskal-Wallis test; p=0.7413).

Figure 14:
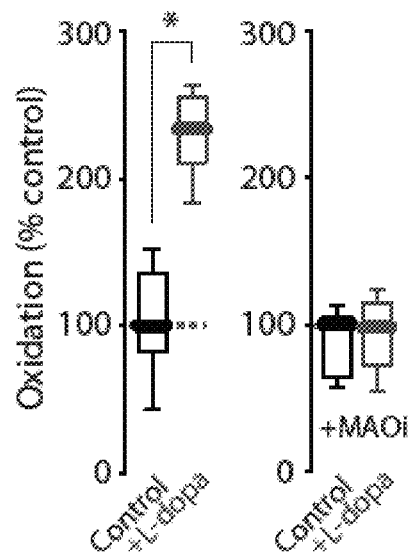
Figure 14:
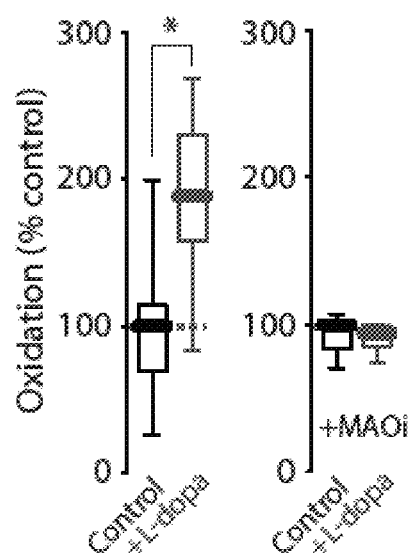

FIG. 14. Levodopa induces monoamine oxidase-dependent mitochondrial stress in dendrites and axons of dopamine differentiated iPSCs. Human-derived iPSCs were generated and transfected with the redox sensitive probe roGFP targeting either the mitochondrial matrix or cytosolic compartment. Basal levels of oxidant stress were measured (control) followed by incubation with 100 μM levodopa (+l-dopa). (Panel A) L-dopa increased axonal mitochondrial stress (left; n=15 axons; Wilcoxon matched-pairs signed rank test; p<0.0001) and was prevented by monoamine oxidase inhibition (right) with 5 μM clorgyline+10 μM rasagiline (+MAOi; Wilcoxon matched-pairs signed rank test; p=0.4973); n=14 axons. (Panel B) Dendritic mitochondrial stress was increased by +1-dopa (right; n=23 dendrites; Wilcoxon matched-pairs signed rank test; p<0.0001) and prevented by +MAOi (right; n=11 dendrites; Wilcoxon matched-pairs signed rank test; p=0.2783); *p<0.05.

Figure 2:
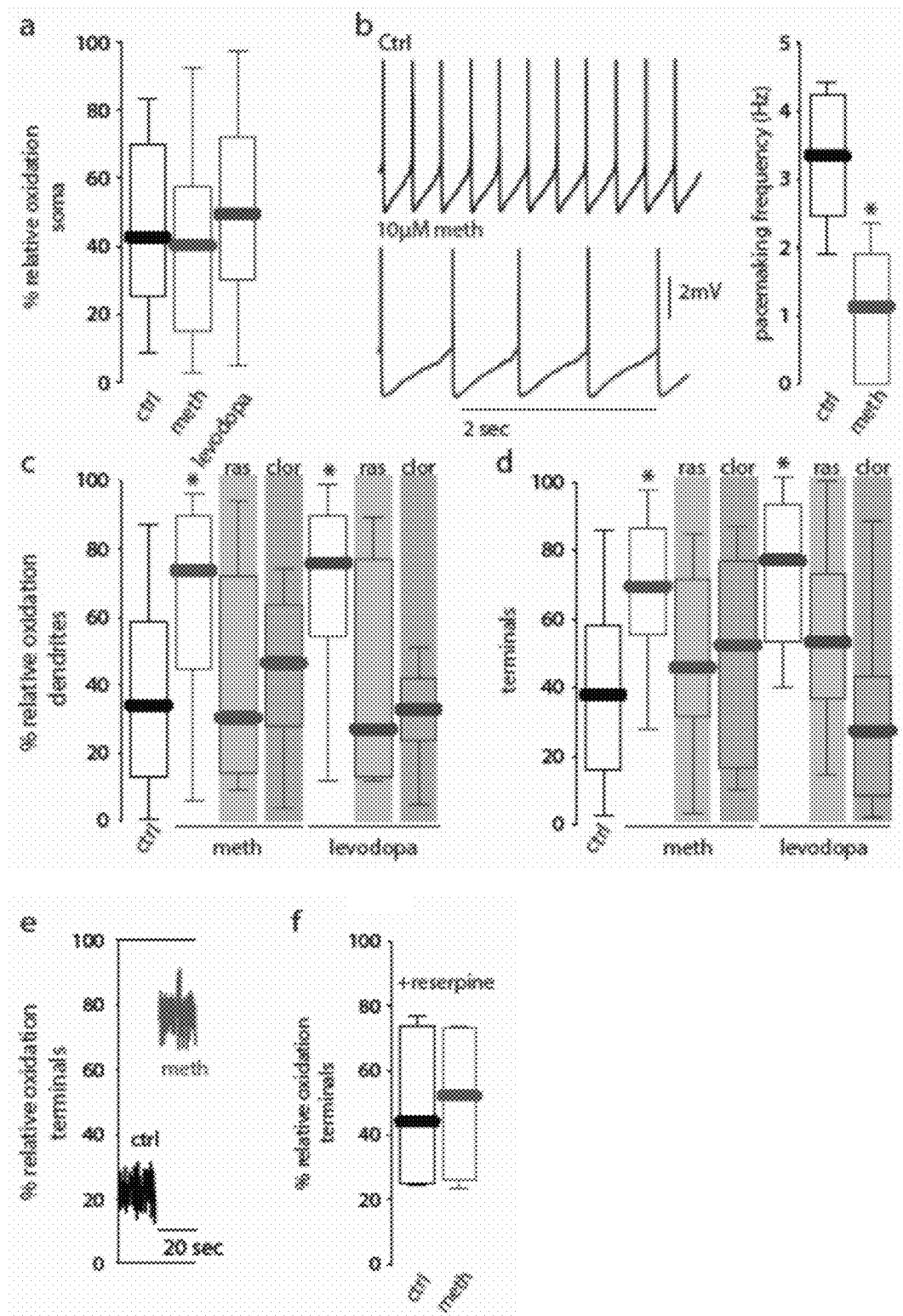
FIG. 2. Mitochondrial stress. Slices were tested with aCSF (ctrl), 10 µM methamphetamine (meth) or 100 µM levodopa. (Panel a) Somatic mitochondrial stress. (Panel b) Pacemaking frequency was attenuated by meth. (Panel c) Mitochondrial stress in dendrites was increased by meth and levodopa but prevented by 10 µM rasagiline (ras; MAO-B inhibitor) and 5 µM clorgyline (clor; MAO-A inhibitor). (Panel d) Terminal stress was increased by meth and levodopa and attenuated by rasagiline and clorgyline. (Panel e) Sample trace of methamphetamine-induced mitochondrial stress. (Panel f) 10 µM meth had no effect on terminal mitochondrial stress in slices from reserpinized mice. $*p<0.05$; n=7-18 cells; n=4-20 slices.
Figure 3:
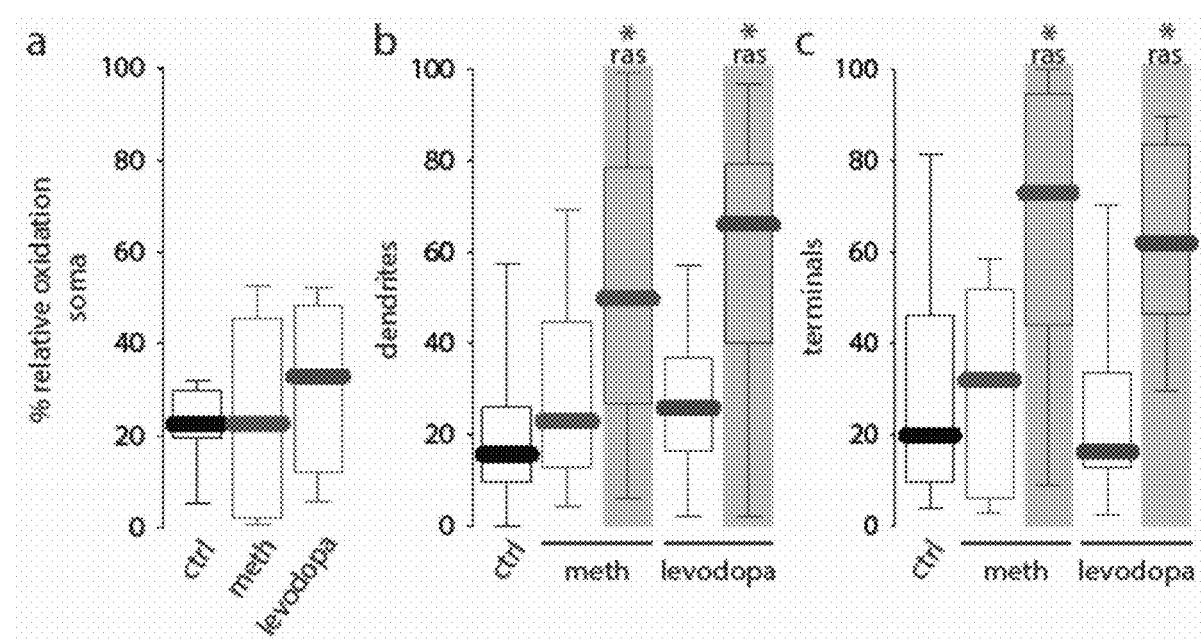
FIG. 3. Cytosolic stress. Slices were tested with aCSF (ctrl), 10 µM methamphetamine (meth) or 100 µM levodopa. (Panel a) cytosolic stress was unaffected by treatment conditions. (Panel b) Dendritic cytosolic stress was only increased by meth and levodopa when monoamine oxidase-B was inhibited by 10 µM rasagiline (ras). (Panel c) Terminal cytosolic stress was only increased by meth and levodopa when monoamine oxidase-B was inhibited by 10 µM rasagiline. $*p<0.05$; n=10-11 cells; n=10-15 slices.
Figure 4:
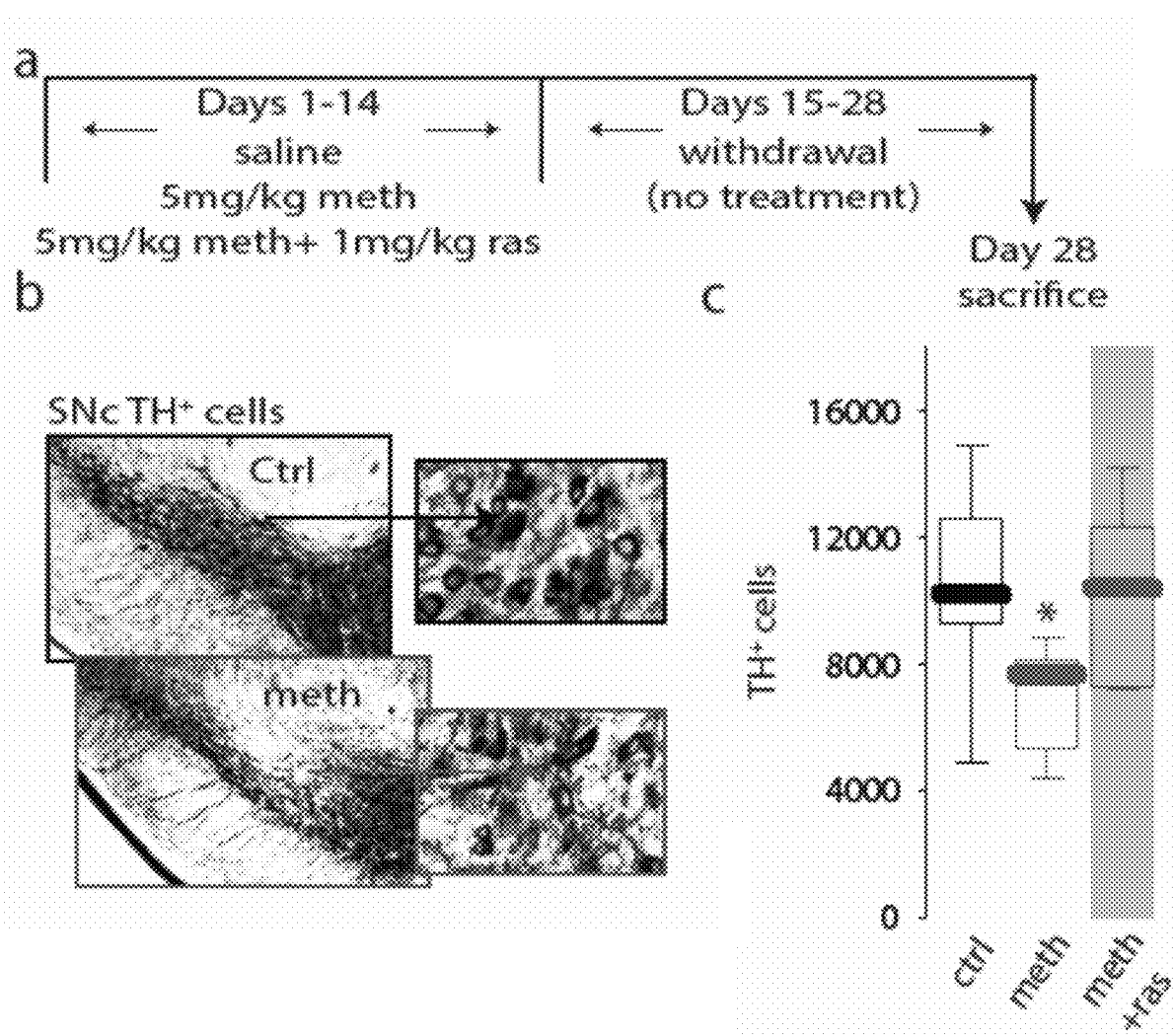
FIG. 4. Methamphetamine-induced loss of tyrosine hyrdroxylase positive cells was prevented by rasagiline. (Panel a) Saline, 5 mg/kg methamphetamine (meth) or meth+1 mg/kg rasagiline (ras; 30 min pretreatment) was administered for 14 days and animals sacrificed after 14 days withdrawal. (Panel b) Sample images depicting meth-induced change in tyrosine hydroxylase positive (TH+) cells. (Panel c) Ras pretreatment prevented meth-induced loss of TH+ cells. $*p<0.05$; n=6-12.
Figure 15:
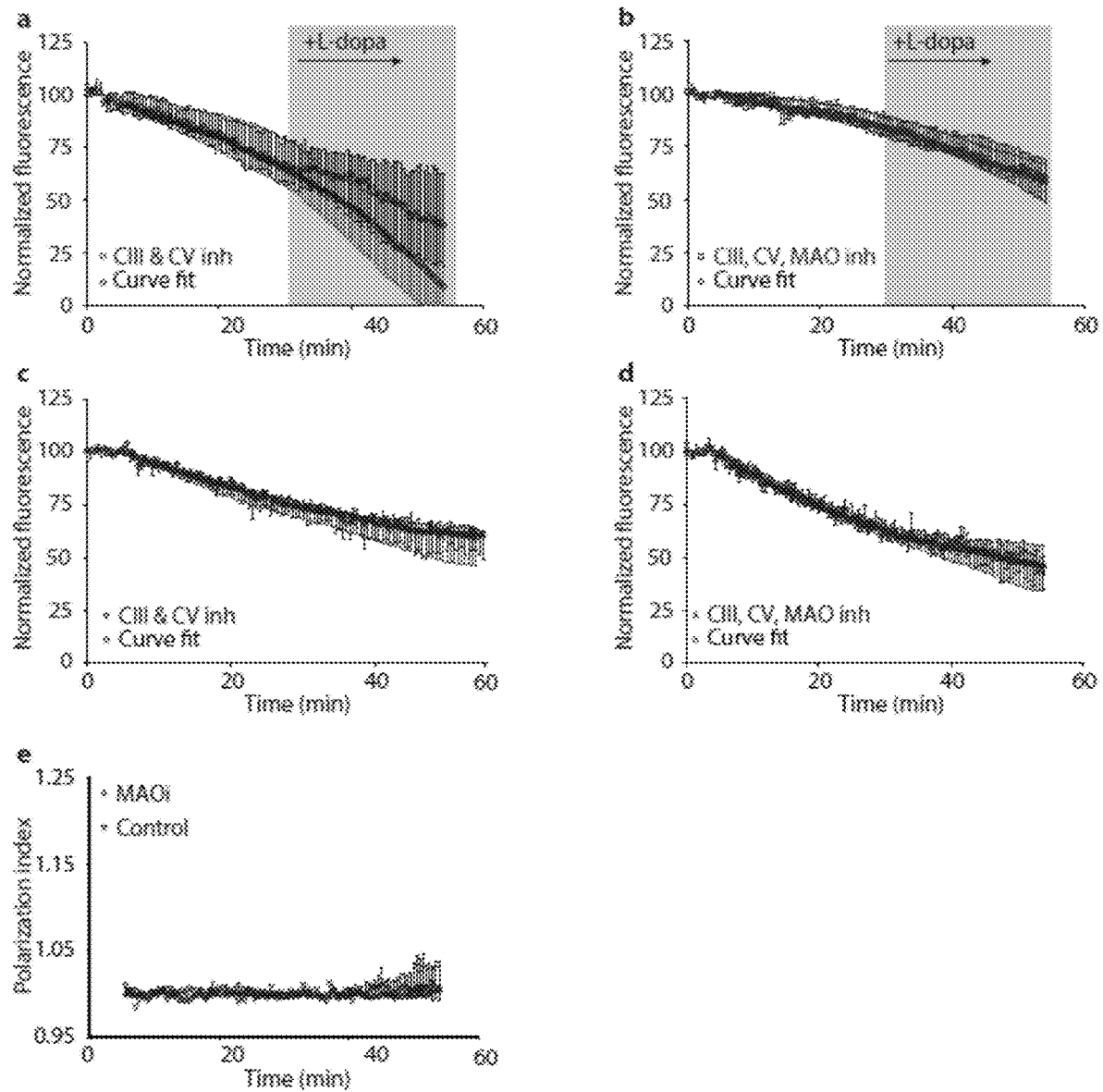

FIG. 15. Mitochondrial membrane potential measured by TMRM. Mitochondrial depolarization was measured using TMRM. Inhibition of complex III (2 μM myxothiazol) and ANT (1 μM carboxyatractyloside) resulted in fluorescent decay. (Panel A) The trajectory of the decay was changed by 100 μM levodopa (+1-dopa) administration at 30 minutes. (Panel B) The +1-dopa effect was MAO dependent, as addition of MAO inhibitors (10 μM rasagiline and 5 μM clorgyline; MAOi) eliminated the augmented signal. (Panels C, D) MAOi did not alter the trajectory of decay induced by inhibition of complex III and ANT. (Panels A-D) Mathematical models (black) were generated for each region of interest with stable background (less than 15% variation in baseline fluorescence) using the first 30 minutes of data, prior to levodopa administration, to fit a polynomial (centered second order polynomial, GraphPad Prism, average $r^2$: 0.93 (Panel A), 0.93 (Panel B), 0.96 (Panel C), 0.94 (Panel D)). Polarization indices (Panel E, FIG. 2 Panel d) were calculated by dividing observed values by modeled ones, allowing for analysis of the alteration of curve trajectory elicited by levodopa administration in the presence and absence of MAOi.

Figure 16:
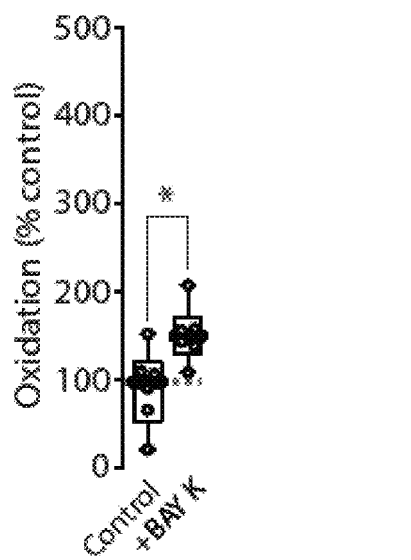
Figure 16:
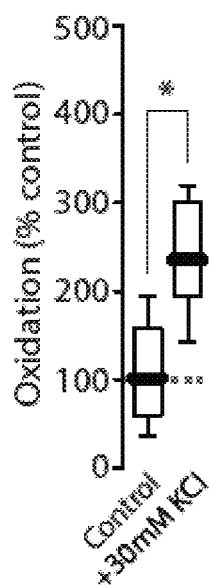

FIG. 16. The L-type channel activator Bay K 8644 and 30 mM KCl increased axonal mitochondrial stress. Ex vivo slices containing the dorsolateral striatum were prepared from mice expressing the redox sensitive probe roGFP in substantia nigra pars compacta dopaminergic neuron axonal mitochondrial matrix tested. (Panel A) The calcium channel activator bay K 8644 (10 μM; +BAY K; n=6 slices/4 mice) increased axonal mitochondrial stress; p=0.026 Mann Whitney test. (Panel B) Perfusion of 30 mM KCl also increased axonal mitochondrial stress (n=11 slices/6 mice); p=0.002 Mann Whitney test; *p<0.05.

Figure 17:
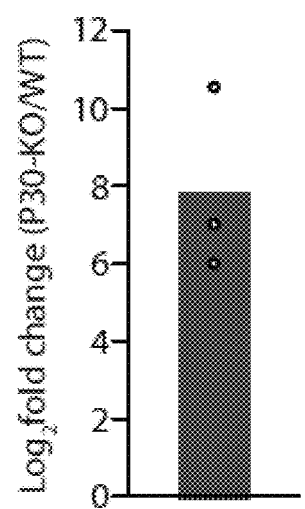

FIG. 17. Loss of RISP in dopaminergic neurons leads to up-regulation of Monoamine oxidase B Mass spectrometry-based in protein analysis. Peptides were analyzed by LC-MS/MS. MAOB peptides are detected in SNC tissue from WT and RISP-KO SNC by mass spectrometry. RISP-KO mice show overexpression of MAOB protein in SNC comparing with WT mice. Data represent the analysis of SNC tissue from 3 WT (DAT-cre⁻ fl/fl) and 3 DAT-RISP-KO (DAT-cre⁺ fl/fl) animals.

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a pharmaceutical agent" is a reference to one or more pharmaceutical agents and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the terms "racemic" and "racemate" refer mixtures of chiral molecules having equal proportions of L- and D-enantiomers.

As used herein, the term "pharmaceutical agent" refers to a compound, macromolecule, or other entity that is administered (e.g., within the context of a pharmaceutical composition) to a subject to elicit a desired biological response. A pharmaceutical agent may be a "drug" or any other material which is biologically active in a human being or other mammal, locally and/or systemically. Examples of drugs are disclosed in the Merck Index and the Physicians Desk Reference, the entire disclosures of which are incorporated by reference herein for all purposes.

As used herein, the term "pharmaceutical formulation" refers to at least one pharmaceutical agent in combination with one or more additional components that assist in rendering the pharmaceutical agent(s) suitable for achieving the desired effect upon administration to a subject. The pharmaceutical formulation may include one or more additives, for example pharmaceutically acceptable excipients, carriers, penetration enhancers, coatings, stabilizers, buffers or other materials physically associated with the pharmaceutical agent to enhance the administration, release (e.g., timing of release), deliverability, bioavailability, effectiveness, etc. of the dosage form. The formulation may be, for example, a liquid, a suspension, a solid, a nanoparticle, emulsion, micelle, ointment, gel, emulsion, coating, etc. A pharmaceutical formulation may contain a single pharmaceutical agent or multiple pharmaceutical agents As used herein, the term "pharmaceutical composition" refers to the combination of one or more pharmaceutical agents with one or more carriers, inert or active, making the composition especially suitable for diagnostic or therapeutic use in vivo, in vivo or ex vivo. A pharmaceutical composition comprises the physical entity that is administered to a subject, and may take the form of a solid, semi-solid or liquid dosage form, such as tablet, capsule, orally-disintegrating tablet, pill, powder, suppository, solution, elixir, syrup, suspension, cream, lozenge, paste, spray, etc. A pharmaceutical composition may comprise a single pharmaceutical agent or multiple pharmaceutical agents. A pharmaceutical composition may comprise a single pharmaceutical formulation (e.g., extended release, immediate release, delayed release, nanoparticulate, etc.) or multiple formulations (e.g., immediate release and delayed release, nanoparticulate and non-nanoparticulate, etc.).

As used herein, the term "sequential release" refers to a release profile for a pharmaceutical composition in which a two or more pharmaceutical agents are released at distinct time-points following administration to a subject. The release time-point may refer to the pharmaceutical agent being absorbed by a subject, entering the blood stream, becoming bioavailable, etc. the time interval between release time-points may be measured from initial release or from the peak release of each pharmaceutical agent. Pharmaceutical agents may have overlap between their release profiles (e.g., 0-4 hours and 2-5 hours) and still be considered sequential release if they exhibit distinct onsets of release or peaks of release. A time interval of about 1 hour is typically required to constitute sequential release. The term "concurrent release" refers to pharmaceutical agents with substantially identical release profiles, onsets of release, and/or peak releases.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfinuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "co-administration" refers to the administration of at least two agents or therapies to a subject. In some embodiments, the co-administration of two or more agents/therapies is concurrent. In other embodiments, the co-administration of two or more agents/therapies is sequential (e.g., a first agent/therapy is administered prior to a second agent/therapy). In some embodiments, the two or more therapies are administered concurrently, but released (e.g., absorbed, become bioavailable, etc.) sequentially. For example, a composition comprising a first agent and a second agent is administered to a subject (e.g., orally), the first agent is released and becomes bioavailable immediately, but the second agent is formulated for delayed release (e.g., enteric release, release 2-8 hours after administration, etc.). Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "therapeutically effective amount" means an amount of a drug effective to facilitate a desired therapeutic effect in a particular class of subject (e.g., infant, child, adolescent, adult).

DETAILED DESCRIPTION

Provided herein are compositions and methods to reduce toxicity resulting from pharmaceutical treatment, that can lead to increased risk of developing Parkinson's disease (PD) and/or acceleration of PD-associated deterioration.

A hallmark of Parkinson's disease is the progressive degeneration of dopamine neurons in the substantia nigra pars compacta (SNc). Experiments indicate that mitochondrial stress is a causal factor contributing to PD pathogenesis, and that methamphetamine/amphetamine treatment increases mitochondrial stress due to dopamine metabolism by monoamine oxidase and opening of Cav1 $Ca^{2+}$ channels, leading to degeneration of dopamine neurons. Experiments conducted during development of embodiments herein demonstrate that this mitochondrial stress and degeneration was effectively attenuated by administration of a monoamine oxidase B inhibitor (e.g., rasagiline) and/or Cav1 inhibitor (e.g., dihydropyridines). In some embodiments, provided herein are compositions to prevent mitochondrial stress and protect SNc dopamine neurons by inhibiting monoamine oxidase B and/or Cav1. In some embodiments, the compositions and methods herein reduce mitochondrial stress induced by methamphetamine/amphetamine use, for example, for the treatment of ADHD. In some embodiments, the compositions and methods herein reduce mitochondrial stress induced by levodopa use, for example, for the treatment of PD.

In some embodiments, provided herein are pharmaceutical combinations comprising at least (a) a therapeutic agent (e.g., a therapeutic agent that induces mitochondrial stress (e.g., amphetamine, methamphetamine, levodopa, etc.), etc.), and (b) a mitochondrial stress reduction agent (e.g., a monoamine oxidase inhibitor (e.g., rasagiline), a Cav1 inhibitor (e.g., dihydropyridines), etc.), and methods of treatment (e.g., of ADHA, of Parkinson's, etc.) and/or reduction of side effects therewith.

In some embodiments, methods, compositions, formulations, etc. described herein provide a therapeutic agent for the treatment or prevention of a disease, condition, or symptoms associated therewith. In some embodiments, the therapeutic agent induces mitochondrial stress.

In some embodiments, the therapeutic agent is amphetamine (e.g., ADZENYS XR-ODT, DYANAVEL XR, EVEKEO, ADDERALL, ADDERALL XR, etc.) or alpha-methylphenethylamine. As used herein, the term "amphetamine" encompasses levoamphetamine (l-amphetamine), dextroamphetamine (d-amphetamine), racemic mixtures of d- and l-amphetamine, and non-racemic mixtures of d- and l-amphetamine (e.g., 75% d-amphetamine and 25% l-amphetamine), and is depicted by the formula:

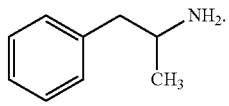

L-amphetamine is depicted by the formula:

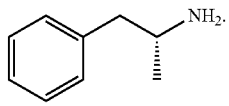

D-amphetamine is depicted by the formula:

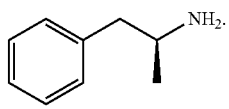

Amphetamine is a potent central nervous system (CNS) stimulant that is used in the treatment of attention deficit hyperactivity disorder (ADHD), narcolepsy, and obesity. Amphetamines are noncatecholamine sympathomimetic amines that promote release of catecholamines (primarily dopamine and norepinephrine) from their storage sites in the presynaptic nerve terminals. A less significant mechanism may include their ability to block the reuptake of catecholamines by competitive inhibition. The anorexigenic effect is probably secondary to the CNS-stimulating effect; the site of action is probably the hypothalamic feeding center. Amphetamine is commercially available as an oral tablet, an oral suspension, an extended release formulation, a disintegrating formulation, etc. In some embodiments, amphetamine is provided in a single dose formulations of 1 to 50 mg (e.g., 1 mg, 2 mg, 3 mg, 3.1 mg, 4 mg, 5 mg, 6 mg, 6.3 mg, 7 mg, 8 mg, 9 mg, 9.4 mg, 10 mg, 12 mg, 12.5 mg, 14 mg, 15.7 mg, 16 mg, 18 mg, 18.8 mg, 20 mg, 25 mg, 30 mg, 35 mg, 40 mg, 45 mg, 50 mg, or ranges therebetween). In some embodiments, multiple doses of amphetamine are provided.

In some embodiments, particularly when administered for the treatment of narcolepsy in an adult, amphetamine is administered in an initial dose of 10 mg orally per day in divided doses (e.g., 2, 3, 4, etc.) and followed by maintenance doses in raised in 10 mg increments at weekly intervals until optimal response is obtained (e.g., 10 mg, 20 mg, 30 mg, 40 mg, 50 mg, etc.); doses are reduced in adverse reactions (e.g., insomnia, anorexia, etc.) are experienced. In some embodiments, the first dose is administered on awakening, and additional doses are given at intervals of 2 to 8 hours (e.g., 2, 3, 4, 5, 6, 7, 8, or ranges therebetween). In some embodiments, a maintenance dose of 5 to 60 mg per day (e.g., 5 mg, 10 mg, 15 mg, 20 mg, 25 mg, 30 mg, 35 mg, 40 mg, 45 mg, 50 mg, 55 mg, 60 mg) in divided doses is utilized.

In some embodiments, particularly when administered for the treatment of obesity in an adult, amphetamine is administered in an initial dose of 5 mg orally 30 to 60 minutes before each meal. In some embodiments, doses are increased to achieve effectiveness, up to about 30 mg orally per day in divided doses. In some embodiments, doses are given at intervals of 2 to 8 hours (e.g., 2, 3, 4, 5, 6, 7, 8, or ranges therebetween). In some embodiments, doses are administered prior to eating (e.g., meals). In some embodiments, particularly when administered for the treatment of obesity, amphetamine is ceased after 15 days, 20 days, 25 days, 30 days, 35 days, 40 days, or more, or ranges therebetween. In some embodiments, doses are reduced if adverse reactions (e.g., insomnia, anorexia, etc.) are experienced.

In some embodiments, amphetamine is administered for the treatment of narcolepsy in a pediatric patient (e.g., child (e.g., 6-11 years old), adolescent (e.g., 12-17 years old), etc.). For treatment of narcolepsy in a patient aged 6-11 years, an initial dose of 5 mg orally per day in divided doses, followed by increases in daily dose of 5 mg increments at weekly intervals until optimal response is obtained (e.g., not to exceed 60 mg daily divided dose). For treatment of narcolepsy in a patient aged 12-17 years, an initial dose of 10 mg orally per day in divided doses, followed by increases in daily dose of 10 mg increments at weekly intervals until optimal response is obtained (e.g., not to exceed 60 mg daily divided dose). In some embodiments, doses are reduced if adverse reactions (e.g., insomnia, anorexia, etc.) are experienced.

In some embodiments, amphetamine is administered for the treatment of obesity in a pediatric patient. For treatment of obesity in a patient aged 12-17 years, an initial dose of 5 mg orally 30 to 60 minutes before each meal is administered, with a maximum dose of 30 mg orally per day in divided doses. In some embodiments, particularly when administered for the treatment of obesity, amphetamine is ceased after 15 days, 20 days, 25 days, 30 days, 35 days, 40 days, or more, or ranges therebetween.

In some embodiments, amphetamine is administered for the treatment of attention deficit hyperactive disorder in a pediatric patient. For a subject 3-5 years old, a dose of 2.5 mg/day orally is administered, with maintenance doses raised in 2.5 mg increments at weekly intervals until optimal response is obtained. For a subject 6-17 years old, a dose of 5 mg is administered orally, once or twice daily. Daily dose may be raised in 5 mg increments at weekly intervals until optimal response is obtained; only exceeding 40 mg per day in rare cases. In some embodiments, for 6-17 year old subjects, and extended release formulation is used. With the extended release formulation, an initial does of 2.5 or 5 mg is administered orally once a day in the morning, and a maintenance dose is raised in increments of 2.5 to 10 mg per day every 4 to 7 days until optimal response is obtained (maximum dose of 20 mg orally per day).

Any of the above dosing regimens for amphetamine may be altered in embodiments herein.

In some embodiments, amphetamine is provided as a racemic mixture. In some embodiments, amphetamine is provided in a d-amphetamine:l-amphetamine ratio of (1:99, 2:98, 3:97, 4:96, 5:95, 10:90, 15:85, 20:80, 25:75, 30:70, 35:65, 40:60, 45:55, or ranges therebetween). In some embodiments, amphetamine is provided in an l-amphetamine:d-amphetamine ratio of (1:99, 2:98, 3:97, 4:96, 5:95, 10:90, 15:85, 20:80, 25:75, 30:70, 35:65, 40:60, 45:55, or ranges therebetween).

In some embodiments, the therapeutic agent is methamphetamine (e.g., DESOXYN). Methamphetamine (contracted from N-methylamphetamine) is a strong central nervous system (CNS) stimulant that is used as a treatment for attention deficit hyperactivity disorder and obesity. As used herein, the term "methamphetamine" encompasses levo-methamphetamine (l-methamphetamine), dextro-methamphetamine (d-methamphetamine), racemic mixtures of d- and l-methamphetamine, and non-racemic mixtures of d- and l-methamphetamine (e.g., 75% d-methamphetamine and 25% l-methamphetamine), and is depicted by the formula:

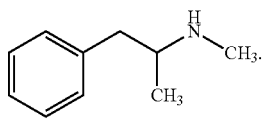

L-methamphetamine is depicted by the formula:

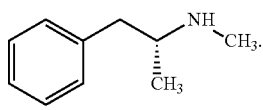

D-methamphetamine is depicted by the formula:

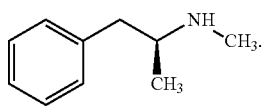

In some embodiments, the therapeutic agent is amphetamine and is provided as a formulation with one or more other therapeutic agents (e.g., dextroamphetamine).

In some embodiments, methamphetamine is provided in a single dose formulations of 1 to 50 mg (e.g., 1 mg, 2 mg, 3 mg, 4 mg, 5 mg, 6 mg, 7 mg, 8 mg, 9 mg, 10 mg, 12 mg, 15 mg, 18 mg, 20 mg, 25 mg, 30 mg, 35 mg, 40 mg, 45 mg, 50 mg, or ranges therebetween). In some embodiments, multiple doses of methamphetamine are provided.

In some embodiments, methamphetamine is administered for the treatment of obesity in adult patients. In some embodiments, particularly when administered for treatment of obesity, methamphetamine is administered in 5 mg doses about 30 minutes before each meal. In some embodiments, methamphetamine is ceased after 15 days, 20 days, 25 days, 30 days, 35 days, 40 days, or more, or ranges therebetween.

In some embodiments, methamphetamine is administered for the treatment of attention deficit disorder (ADD) and/or attention deficit hyperactive disorder (ADHD) in pediatric patients. In some embodiments, particularly when administered for treatment of ADD and/or ADHD, methamphetamine is initially administered in 5 mg doses once or twice daily, with maintenance doses being raised in increments of 5 mg at weekly intervals until an optimum clinical response is achieved, with a typical effective dose of 15 to 30 mg per day.

In some embodiments, methamphetamine is administered for the treatment of obesity in pediatric patients. In some embodiments, particularly when administered for treatment of obesity, methamphetamine is administered in 5 mg doses about 30 minutes before each meal. In some embodiments, methamphetamine is ceased after 15 days, 20 days, 25 days, 30 days, 35 days, 40 days, or more, or ranges therebetween.

Any of the above dosing regimens for methamphetamine may be altered in embodiments herein.

In some embodiments, methamphetamine is provided as a racemic mixture. In some embodiments, methamphetamine is provided in a d-methamphetamine:l-methamphetamine ratio of (1:99, 2:98, 3:97, 4:96, 5:95, 10:90, 15:85, 20:80, 25:75, 30:70, 35:65, 40:60, 45:55, or ranges therebetween). In some embodiments, methamphetamine is provided in an l-methamphetamine:d-methamphetamine ratio of (1:99, 2:98, 3:97, 4:96, 5:95, 10:90, 15:85, 20:80, 25:75, 30:70, 35:65, 40:60, 45:55, or ranges therebetween). In some embodiments, methamphetamine is provided as 100% l-methamphetamine. In some embodiments, methamphetamine is provided as 100% d-methamphetamine.

In some embodiments, the therapeutic agent is levodopa (L-DOPA, L-3,4-dihydroxyphenylalanine). L-DOPA is the precursor to the neurotransmitters dopamine, norepinephrine (noradrenaline), and epinephrine (adrenaline) collectively known as catecholamines. L-DOPA itself mediates neurotrophic factor release by the brain and CNS. L-DOPA is manufactured in a pure form and is sold as a psychoactive drug (SINEMET, PHARMACOPA, ATAMET, STALEVO, MADOPAR, PROLOPA, etc.). Levodopa is depicted by the chemical formula:

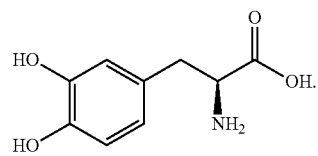 [SMILES: N[C@@H](Cc1ccc(O)c(O)c1)C(=O)O]

As a therapeutic, L-DOPA is commonly used in the clinical treatment of Parkinson's disease and dopamine-responsive dystonia. Levodopa is used alone or in combination with carbidopa to treat Parkinson's disease; some patients benefit from the combination of medicine, while others benefit from levodopa alone. In some embodiments, the therapeutic agent in compositions and methods herein comprises levodopa and carbidopa.

Levodopa is commercially available as an oral tablet or capsule. In some embodiments, levodopa is provided in a single dose formulations of 1 to 50 mg (e.g., 1 mg, 2 mg, 3 mg, 3.1 mg, 4 mg, 5 mg, 6 mg, 6.3 mg, 7 mg, 8 mg, 9 mg, 9.4 mg, 10 mg, 12 mg, 12.5 mg, 14 mg, 15.7 mg, 16 mg, 18 mg, 18.8 mg, 20 mg, 25 mg, 30 mg, 35 mg, 40 mg, 45 mg, 50 mg, or ranges therebetween). In some embodiments, multiple doses of amphetamine are provided.

In some embodiments, particularly when administered for the treatment of Parkinson's in an adult, amphetamine is levodopa in an initial dose of 200-600 mg (e.g., 200 mg, 250 mg, 300 mg, 350 mg, 400 mg, 450 mg, 500 mg, 550 mg, 600 mg, or ranges therebetween) orally twice a day (e.g., with meals). In some embodiments, for maintenance, doses are increased to 1000 to 6000 mg (e.g., 1000 mg, 2000 mg, 3000 mg, 4000 mg, 5000 mg, 6000 mg, or more, or ranges therebetween).

In some embodiments, particularly when administered for the treatment of restless leg syndrome in an adult, levodopa is administered in a dose of 25 to 100 mg (e.g., 25 mg, 50 mg, 75 mg, 100 mg, or ranges therebetween) 1 to 2 hours before bedtime (e.g., administered with a dopa-decarboxylase inhibitor).

In some embodiments, any therapeutic agent that induces mitochondrial stress may find use in embodiments herein. Such therapeutic agents may include, but are not limited to, anticonvulsants (e.g., valproate (DEPAKOTE)), antidepressants (e.g., amitriptyline (ELAVIL), amoxapine, fluoxetine (PROZAC), citalopram (CIPRAMIL), etc.), antipsychotics (e.g., chlorpromazine (THORAZINE), fluphenazine (PROLIXIN), haloperidol (HALDOL), resperidone (RISPERDOL), etc.), barbituates (e.g., phenobarbital, secobarbital (SECONAL), butalbital (FIORINAL), amobarbital (AMYTAL), pentobarbital (NEMBUTAL), etc.), anxiety medications (e.g., alprazolam (XANAX), diazepam (VALIUM, DIASTAT), etc.), cholesterol medications (e.g., statins, bile acids-cholestyramine, ciprofibrate, etc.), analgesics/anti-inflammatory medications (e.g., asprin, acetaminophen, indomethacin, maproxen, diclofenac, etc.), antibiotics (e.g., tetracycline, minocycline, chloramphenical, aminoglycosides, linezolid (ZYVOX), etc.), amiodarone, steroids, interferon, zidovudine,c medications (e.g., doxorubicine (ADRIAMYCIN), cis-platinum, tamoxifen, etc.), metformin, beta-blockers, etc.

In some embodiments, methods, compositions, formulations, etc. described herein provide a mitochondrial stress reduction agent for the alleviation of side-effects caused by the treatment or prevention of a disease, condition, or symptoms associated therewith.

In some embodiments, the mitochondrial stress reduction agent is a monoamine oxidase (MAO) inhibitor (MAOI). MAOIs typically act by inhibiting the activity of one or more enzymes of the monoamine oxidase family. There are two isoforms of monoamine oxidase, MAO-A and MAO-B. MAO-A preferentially deaminates serotonin, melatonin, epinephrine, and norepinephrine. MAO-B preferentially deaminates phenethylamine and certain other trace amines. Dopamine is equally deaminated by both types. MAOIs differ in terms of reversibility and selectivity. Nonselective MAO-A/MAO-B inhibitors include, but are not limited to, hydrazines (e.g., isocarboxazid (MARPLAN), nialamide (NIAMID), phenelzine (NARDIL, NARDELZINE), hydracarbazine, benmoxin (NERUSIL, NEURALEX), iproclozide (SURSUM) iproniazid (MARSILID, IPROZID, IPRONID, RIVIVOL, PROPILNIAZIDA), mebanazine (ACTOMOL), octamoxin (XIMAOL, NIMAOL), pheniprazine (CATRON), phenoxypropazine (DRAZINE), pivalylbenzhydrazine (TERSAVID), safrazine (SAFRA), etc.), non-hydrazines (e.g., tranylcypromine (PARNATE, JATROSOM), caroxazone (SURODIL, TIMOSTENIL), etc.), etc. Selective MAO-A inhibitors include, but are not limited to, bifemelane (ALNERT, CELEPORT), moclobemide (AURORIX, MANERIX), pirlindole (PIRAZIDOL), toloxatone (HUMORYL), minaprine (CANTOR), etc. Selective MAO-B inhibitors include, but are not limited to, rasagiline (AZILECT) and selegiline (DEPRENYL, ELDEPRYL, EMSAM, ZELAPAR). Any suitable MAOIs (e.g., MAO-A selective, MAO-B selective, non-selective) may find use in embodiments herein.

In some embodiments, the mitochondrial stress reduction agent is a calcium channel blocker. In some embodiments, the mitochondrial stress reduction agent is a Cav1 inhibitor. In some embodiments, the mitochondrial stress reduction agent is a dihydropyridine (DHP) class calcium channel blocker (e.g., Cav1 inhibitor). In some embodiments, suitable dihydropyridine class agents include, but are not limited to, amlodipine (NORVASC), aranidipine (SAPRESTA), azelnidipine (CALBLOCK), barnidipine (HYPOCA), benidipine (CONIEL), cilnidipine (ATELEC, CINALONG, SISCARD), clevidipine (CLEVIPREX), isradipine (DYNACIRC, PRESCAL), efonidipine (LANDEL), felodipine (PLENDIL), lacidipine (MOTENS, LACIPIL), lercanidipine (ZANIDIP), manidipine (CALSLOT, MADIPINE), nicardipine (CARDENE, CARDEN SR), nifedipine (PROCARDIA, ADALAT), nilvadipine (NIVADIL), nimodipine (NIMOTOP), nisoldipine (BAYMYCARD, SULAR, SYSCOR), nitrendipine (CARDIF, NITREPIN, BAYLOTENSIN), pranidipine (ACALAS), etc.

In some embodiments, methods are provided herein for the treatment of disease/condition/symptom while eliminating/reducing one or more side effects associated with the therapeutic agent used for such treatment. In some embodiments, methods comprise administration of at least one therapeutic agent and at least one mitochondrial stress reduction agent. In some embodiments, the therapeutic agent and the mitochondrial stress reduction agent are co-administered.

In some embodiments, the therapeutic agent and the mitochondrial stress reduction agent are provided within a single pharmaceutical composition. In some embodiments, the therapeutic agent and the mitochondrial stress reduction agent are provided in a single formulation within a single pharmaceutical composition. In some embodiments the therapeutic agent and the mitochondrial stress reduction agent are provided as separate formulations (e.g., immediate release and delayed release, etc.) within a single pharmaceutical composition. In some embodiments, the therapeutic agent and the mitochondrial stress reduction agent are provided as separate pharmaceutical compositions, but are administered simultaneously or concurrently. In some embodiments, the therapeutic agent and the mitochondrial stress reduction agent are provided as separate pharmaceutical compositions and are administered according to separate dosing schedules and/or with a delay (e.g., minutes, hours, days, etc.) between administrations.

In some embodiments, a pharmaceutical composition comprises a therapeutic agent and a mitochondrial stress reduction agent co-formulated in a single pharmaceutical formulation (e.g., immediate-release, delayed-release, enteric release, nanoparticulate, oral administration, etc.). In some embodiments, a single pharmaceutical formulation comprises amphetamine as the therapeutic agent and an MAOI (e.g., MAO-A inhibitor, MAO-B inhibitor, non-selective MAO inhibitor, etc.) as the mitochondrial stress reduction agent. In some embodiments, a single pharmaceutical formulation comprises methamphetamine as the therapeutic agent and an MAOI (e.g., MAO-A inhibitor, MAO-B inhibitor, non-selective MAO inhibitor, etc.) as the mitochondrial stress reduction agent. In some embodiments, a single pharmaceutical formulation comprises levodopa as the therapeutic agent and an MAOI (e.g., MAO-A inhibitor, MAO-B inhibitor, non-selective MAO inhibitor, etc.) as the mitochondrial stress reduction agent. In some embodiments, a single pharmaceutical formulation comprises amphetamine as the therapeutic agent and rasagiline as the mitochondrial stress reduction agent. In some embodiments, a single pharmaceutical formulation comprises methamphetamine as the therapeutic agent and rasagiline as the mitochondrial stress reduction agent. In some embodiments, a single pharmaceutical formulation comprises levodopa as the therapeutic agent and rasagiline as the mitochondrial stress reduction agent. In some embodiments, a single pharmaceutical formulation comprises amphetamine as the therapeutic agent and a Cav1 inhibitor as the mitochondrial stress reduction agent. In some embodiments, a single pharmaceutical formulation comprises methamphetamine as the therapeutic agent and a Cav1 inhibitor as the mitochondrial stress reduction agent. In some embodiments, a single pharmaceutical formulation comprises levodopa as the therapeutic agent and a Cav1 inhibitor as the mitochondrial stress reduction agent. In some embodiments, a single pharmaceutical formulation comprises amphetamine as the therapeutic agent and a dihydropyridine as the mitochondrial stress reduction agent. In some embodiments, a single pharmaceutical formulation comprises methamphetamine as the therapeutic agent and a dihydropyridine as the mitochondrial stress reduction agent. In some embodiments, a single pharmaceutical formulation comprises levodopa as the therapeutic agent and a dihydropyridine as the mitochondrial stress reduction agent.

In some embodiments, a pharmaceutical composition comprises a first formulation comprising a therapeutic agent and a second formulation comprising a mitochondrial stress reduction agent. In some embodiments, the first formulation is formulated for immediate-release, delayed-release, enteric release, oral administration, etc. In some embodiments, the second formulation is formulated for immediate-release, delayed-release, enteric release, oral administration, etc. In some embodiments, the first formulation comprises amphetamine as the therapeutic agent and the second formulation comprises an MAOI (e.g., MAO-A inhibitor, MAO-B inhibitor, non-selective MAO inhibitor, etc.) as the mitochondrial stress reduction agent. In some embodiments, the first formulation comprises methamphetamine as a therapeutic agent and the second formulation comprises an MAOI (e.g., MAO-A inhibitor, MAO-B inhibitor, non-selective MAO inhibitor, etc.) as the mitochondrial stress reduction agent. In some embodiments, the first formulation comprises levodopa as the therapeutic agent and the second formulation comprises an MAOI (e.g., MAO-A inhibitor, MAO-B inhibitor, non-selective MAO inhibitor, etc.) as the mitochondrial stress reduction agent. In some embodiments, the first formulation comprises amphetamine as the therapeutic agent and the second formulation comprises rasagiline as the mitochondrial stress reduction agent. In some embodiments, the first formulation comprises methamphetamine as the therapeutic agent and the second formulation comprises rasagiline as the mitochondrial stress reduction agent. In some embodiments, the first formulation comprises levodopa as the therapeutic agent and the second formulation comprises rasagiline as the mitochondrial stress reduction agent. In some embodiments, the first formulation comprises amphetamine as the therapeutic agent and the second formulation comprises a Cav1 inhibitor as the mitochondrial stress reduction agent. In some embodiments, the first formulation comprises methamphetamine as the therapeutic agent and the second formulation comprises a Cav1 inhibitor as the mitochondrial stress reduction agent. In some embodiments, the first formulation comprises levodopa as the therapeutic agent and the second formulation comprises a Cav1 inhibitor as the mitochondrial stress reduction agent. In some embodiments, the first formulation comprises amphetamine as the therapeutic agent and the second formulation comprises a dihydropyridine as the mitochondrial stress reduction agent. In some embodiments, the first formulation comprises methamphetamine as the therapeutic agent and the second formulation comprises a dihydropyridine as the mitochondrial stress reduction agent. In some embodiments, the first formulation comprises levodopa as the therapeutic agent and the second formulation comprises a dihydropyridine as the mitochondrial stress reduction agent.

In some embodiments, a first pharmaceutical composition comprises a therapeutic agent and a second pharmaceutical composition comprises a mitochondrial stress reduction agent. The first pharmaceutical composition is formulated for immediate-release, delayed-release, enteric release, oral administration, etc. In some embodiments, the second pharmaceutical composition is formulated for immediate-release, delayed-release, enteric release, oral administration, etc. the first and second pharmaceutical compositions may be formulated for the same or different routes of administration and may be for concurrent, sequential, and/or separate administration (e.g., separated by minutes, hours, days, etc.). In some embodiments, the first pharmaceutical composition comprises amphetamine as the therapeutic agent and the second pharmaceutical composition comprises an MAOI (e.g., MAO-A inhibitor, MAO-B inhibitor, non-selective MAO inhibitor, etc.) as the mitochondrial stress reduction agent. In some embodiments, the first pharmaceutical composition comprises methamphetamine as a therapeutic agent and the second pharmaceutical composition comprises an MAOI (e.g., MAO-A inhibitor, MAO-B inhibitor, non-selective MAO inhibitor, etc.) as the mitochondrial stress reduction agent. In some embodiments, the first pharmaceutical composition comprises levodopa as the therapeutic agent and the second pharmaceutical composition comprises an MAOI (e.g., MAO-A inhibitor, MAO-B inhibitor, non-selective MAO inhibitor, etc.) as the mitochondrial stress reduction agent. In some embodiments, the first pharmaceutical composition comprises amphetamine as the therapeutic agent and the second pharmaceutical composition comprises rasagiline as the mitochondrial stress reduction agent. In some embodiments, the first pharmaceutical composition comprises methamphetamine as the therapeutic agent and the second pharmaceutical composition comprises rasagiline as the mitochondrial stress reduction agent. In some embodiments, the first pharmaceutical composition comprises levodopa as the therapeutic agent and the second pharmaceutical composition comprises rasagiline as the mitochondrial stress reduction agent. In some embodiments, the first pharmaceutical composition comprises amphetamine as the therapeutic agent and the second pharmaceutical composition comprises a Cav1 inhibitor as the mitochondrial stress reduction agent. In some embodiments, the first pharmaceutical composition comprises methamphetamine as the therapeutic agent and the second pharmaceutical composition comprises a Cav1 inhibitor as the mitochondrial stress reduction agent. In some embodiments, the first pharmaceutical composition comprises levodopa as the therapeutic agent and the second pharmaceutical composition comprises a Cav1 inhibitor as the mitochondrial stress reduction agent. In some embodiments, the first pharmaceutical composition comprises amphetamine as the therapeutic agent and the second pharmaceutical composition comprises a dihydropyridine (e.g., isradipine) as the mitochondrial stress reduction agent. In some embodiments, the first pharmaceutical composition comprises methamphetamine as the therapeutic agent and the second pharmaceutical composition comprises a dihydropyridine (e.g., isradipine) as the mitochondrial stress reduction agent. In some embodiments, the first pharmaceutical composition comprises levodopa as the therapeutic agent and the second pharmaceutical composition comprises a dihydropyridine (e.g., isradipine) as the mitochondrial stress reduction agent.

It is generally contemplated that the compositions and/or pharmaceutical combinations according to the technology provided are formulated for administration to a mammal, and especially to a human with a condition that is responsive to the administration of such compounds. Therefore, where contemplated compounds are administered in a pharmacological composition or combination, it is contemplated that a formulation may be in the form of an admixture with a pharmaceutically acceptable carrier. For example, contemplated compounds and combinations can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents for treating obesity and related disorders, including, but not limited to insulin resistance, diabetes, steatosis, nonalcoholic steatotic hepatitis, and atherosclerosis.

With respect to administration to a subject, it is contemplated that the compounds and/or combinations be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual clinician to achieve the desired therapeutic goal.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (e.g., dosage).

Pharmaceutical preparations for oral administration include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Therapeutic compositions formulated in a pharmaceutical acceptable carrier may be prepared, placed in an appropriate container, and labeled for treatment of the indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

Accordingly, in some embodiments, the composition (comprising one agent or a pharmaceutical composition) is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of therapeutic agents over time.

In some embodiments, the pharmaceutical preparations and/or formulations of the technology are provided in particles. Particles as used herein means nanoparticles or microparticles (or in some instances larger) that can consist in whole or in part of the therapeutic agents as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, nonerodible, biodegradable, or nonbiodegradable material or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in Macromolecules, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

In some embodiments, the pharmaceutical compositions are formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, a therapeutically effective dose may be estimated initially from cell culture assays and/or animal models (particularly murine models). A therapeutically effective dose refers to that amount that effectively addresses and underlying cause and/or ameliorates symptoms of the disease state or unwanted condition. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. The exact dosage is chosen by the individual clinician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination (s), reaction sensitivities, and tolerance/response to therapy. Long acting pharmaceutical compositions might be administered every 3 to 4 days, every week, or once every two weeks depending on half-life and clearance rate of the particular formulation.

Typical dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; 5,225,212; WO2004/097009, or WO2005/075465, each of which are herein incorporated by reference).

In some embodiments, the therapies disclosed herein are combined or used in combination with other agents useful in the treatment of a disease or condition (e.g., ADD, ADHD, obesity, narcolepsy, Parkinson's disease, etc). Or, by way of example only, the therapeutic effectiveness of one of the therapies described herein may be enhanced by administration of an adjuvant (e.g., by itself the adjuvant may only have minimal therapeutic benefit, but in combination with another therapeutic agent, the overall therapeutic benefit to the patient is enhanced). Such other agents, adjuvants, or drugs, may be administered, by a route (e.g., oral, intravenous, inhalation, etc.) and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

The drug combinations, pharmaceutical compositions, pharmaceutical formulation, dosing regimens, etc. described herein find use in the treatment of various conditions and diseases (e.g., ADD, ADHD, Parkinson's, obesity, narcolepsy, etc.) while reducing/minimizing/eliminating side effects (e.g., mitochondrial stress, Parkinson's disease risk, etc.) associated with such treatment (e.g., side effects associated with the therapeutic agents used in embodiments herein (e.g., levodopa, amphetamine, methamphetamine, etc.).

EXPERIMENTAL

Example 1

Methods

Animals and treatment paradigms: Male C57/B16 and TH-mitoroGFP (Guzman et al., 2010 Nature p. 696; incorporated by reference in its entirety) mice 5-8 wks of age were used for all imaging studies. In addition to the TH-mitoroGFP transgenic line, roGFP was virally delivered into the SNc of C57/B16 mice (either targeting cytosolic or mitochondrial compartments). For dopamine depletion experiments, mice were administered 5 mg/kg reserpine for 5 consecutive days and sacrificed on the 5th day (Day et al., 2006 Nat Neurosci p. 251; incorporated by reference in its entirety). For stereological investigations, mice were administered saline, 5 mg/kg methamphetamine, or 5 mg/kg methamphetamine with a 30 min pretreatment of 1 mg/kg rasagiline for 14 consecutive days and sacrificed after 14 days withdrawal.

Two photon microscopy: Ex vivo slices of the dorsolateral striatum or SNc were prepared and redox status determined as previously described (Guzman et al., 2010 Nature p. 696; incorporated by reference in its entirety). Oxidant stress was measured in control slices, with bath application of 10 µM methamphetamine or preincubated with 100 µM levodopa. The dynamic range of the probe was determined by perfusing 2 mM dithiothreitol (DTT) to fully reduce the probe and 200 µM aldrithiol to fully oxidize the probe; data presented as % relative oxidation.

Stereology: Brains were fixed with 4% paraformaldehyde and serial coronal sections (60 µM) were stained for tyrosine hydroxylase. Total number of tyrosine hydroxylase positive cells were counted in the SNc with the optical fractionator method (West et al., 1991 Anat Rec p. 482; Ilijic et al., 2011 Neurobiol Dis p. 364; incorporated by reference in their entireties).

Results

Experiments conducted during development of embodiments herein demonstrate that methamphetamine and levodopa selectively increased mitochondrial stress at dopamine release sites. The induced stress was absent in reserpinized mice, indicating that dopamine was necessary for the induction of stress. The induced stress was also dependent upon monoamine oxidase enzymes. Both monoamine oxidase-B inhibitor (e.g., rasagiline) and monoamine oxidase-A inhibitor (e.g., clorgyline) attenuated methamphetamine- and levodopa-induced mitochondrial stress. Experiments demonstrate that cytosolic stress was unaffected by methamphetamine and levodopa. Under conditions of monoamine oxidase-B inhibition, cytosolic stress was increased by methamphetamine and levodopa.

Example 2

Methods

Animals: Male mice expressing the redox sensitive roGFP probe targeting the mitochondrial matrix under the tyrosine hydroxylase regulatory element,[10] DAT-cre-Risp (genetic deletion of Rieske iron-sulfur protein, Uqcrfs1), monoamine oxidase AB knockout,[14] DAT bacTRAP,[22] TdTomato under the dopamine transporter regulatory element (DAT-cre X Ai14) and wild-type mice (C57/Bl6) were bred in-house and used with approval by the Northwestern and Rockefeller University Animal Care and Use Committees and in accordance with the National Institutes of Health Guide for the Care and Use of Laboratory Animals. All transgenic subjects were hemizygous for transgenes. Animals were group housed with food and water provided ad libitum on a 12 hour light/dark cycle and sacrificed between 5 and 10 weeks of age for all experiments with the exception of DAT bacTRAP mice used for sequencing which were sacrificed at 4 months of age.

Stereotaxic surgery: PCR amplified roGFP, mitoroGFP and IMSroGFP inserts were subcloned into pFB-TH-SV40pA vector between EcoR1 and SalI sites. After sequence and expression verification, pFB-TH-roGFP vectors were packaged into rAAVs using serotype 9 with titers 2.1-×10$^{13}$ viral genome copies/ml (Virovek). Mice were anesthetized using an isoflurane precision vaporizer (Smiths Medical PM) and placed in a stereotaxic frame (David Kopf Instruments) with a Cunningham adaptor (Harvard Apparatus) to maintain anesthesia delivery throughout surgery. After exposing the skull, a small hole was drilled and 350 nL of AAV9-TH-cytosolic roGFP or AAV9-TH-mitoroGFP delivered via a glass micropipette (Drummond Scientific Company) pulled on a Sutter P-97 puller. The substantia nigra pars compacta (SNc) was targeted at the following coordinates: AP: −3.05, ML: 1.20, and DV −4.30. All surgeries were performed in wild-type mice. Experiments in animals with stereotaxic delivery of AAV viral vectors were performed after at least 10 days post-op.

Ex vivo slice preparation: Mice were terminally anesthetized with a mixture of ketamine (50 mg/kg)/xylazine (4.5 mg/kg) and transcardially perfused with ice cold modified artificial cerebrospinal fluid (aCSF) containing in mM: 124.0 NaCl, 3.0 KCl, 1.0 $CaCl_2$, 2.0 $MgCl_2$, 26 $NaHCO_3$, 1.0 $NaH_2PO_4$, and 16.66 glucose. Once perfused the brain was rapidly removed and either saggital or coronal slices containing the dorsolateral striatum (275 µm thick) or the SNc (220 µm thick) sectioned using a vibratome (VT1200S Leica Microsystems). Slices were transferred to a holding chamber containing normal aCSF containing in mM: 124.0 NaCl, 3.0 KCl, 2.0 $CaCl_2$, 1.0 $MgCl_2$, 26 $NaHCO_3$, 1.0 $NaH_2PO_4$, and 16.66 glucose and allowed at least 30-40 minutes to recover prior to experiments. All solutions were pH 7.4, 310-320 mOsm and continually bubbled with 95% $O_2$/5% $CO_2$.

Ex vivo redox measurements and two photon microscopy: Oxidant stress was assessed using the redox sensitive roGFP probe targeted either to the cytosol or mitochondrial matrix as previously described.[10] Slices were transferred to a recording chamber and continuously perfused with normal aCSF at 32-34° C. Fluorescence was measured using an Ultima Laser Scanning Microscope system (Bruker) with a DODT contrast detector to provide bright-field transmission images with an Olympus 60/0.9NA lens. A two-photon laser (Chameleon Ultra II, Coherent Inc.) tuned to 920 nm was used to excite roGFP. Time series image acquisitions of the roGFP probe were obtained with 60 frames obtained over ~20 seconds with 0.195 µm×0.195 µm pixels and 10-12 µsec dwell times. The dynamic range of the probe was determined with 2 mM dithiothreitol, a reducing agent, and 200 µM aldrithiol, an oxidizing agent, which were sequentially perfused and t-series acquired with each to determine the maximal and minimal fluorescence intensity. Test measurements were calculated as relative oxidation. T-series were analyzed offline and fluorescence measurements in multiple regions of interest evaluated with background subtracted.[10] Final data is presented as percent of control (aCSF perfusion).

Human iPSC culture and neural differentiation: The iPSC line was generated from skin fibroblasts of a healthy individual through retroviral expression of OCT4, SOX2, cMYC, KLF4 and previously clinically characterized.[23-25] Differentiation of iPSCs into midbrain dopaminergic neurons was done according to published protocols.[26] To help control neuralization variability, cells were passaged en bloc (size of 1-2 mm) between days 11 and 14, followed by plating onto poly-d-lysine (PDL)/laminin coated 10 cm dishes. Between days 25 and 30, neural blocks were passed by accutase treatment onto PDL/laminin coated culture dishes. Neuralization growth factors were withdrawn at day 40 and neurons were maintained in Neurobasal media (Life Technologies) containing Neurocult SM1 (Stemcell technologies).

iPSC redox measurements and one photon microscopy: Human iPSC-derived dopaminergic neurons were grown on 12 mm glass coverslips and imaged between 75 and 88 days post-differentiation. Two to four days before experimentation, dopaminergic neurons were infected with viral vectors targeting roGFP expression to mitochondrial matrix (AAV9-TH-mitoroGFP), mitochondrial intermembrane space (AAV9-TH-IMSroGFP),[17] or the cytosol (AAV9-TH-cytoroGFP)[7]. Cultures were transferred to an imaging chamber mounted on an inverted epifluorescence microscope (Nikon TE300) with a 40×/1.35NA oil-immersion objective. The imaging chamber was superfused with aCSF at a flow rate of 1 ml/min. Imaging experiments were carried out at 31-33° C. Cells were illuminated by Polychrome V (TILL Photonics) and emissions were captured with a cooled CCD camera (Hamamatsu ImagEM) and Slidebook imaging software (Intelligent Imaging Innovations). Regions of interests in the dendrites or axon were selected for image analysis. For roGFP redox measurements, cells were exposed at two wavelengths (410 and 470 nm) sequentially for 50 ms each, time-lapse ratiometric images (F410/F470) were captured every 30 sec. dopaminergic neurons expressing roGFP probes were imaged for 15 min to establish stable baselines; the perfusion buffer then switched to aCSF containing 100 µM levodopa for 30 min, or 10 µM rasagiline/5 µM clorigyline for 30 min followed by 100 µM levodopa+10 µM rasagiline/5 µM clorigyline for 30 min. Afterwards, neurons were perfused with 2 mM dithiothreitol for 20 min and then 100 µM aldrithiol for 20 min to obtain full roGFP dynamic range.[7]

To monitor changes in mitochondria membrane potential, dopaminergic neurons were loaded with 20 nM TMRM for 45 min, washed, and maintained in 2 nM TMRM during imaging. Cells were exposed at 550 nm for 50 ms, and time-lapse images were captured every 30 sec. After imaging approximately 15 min to establish stable baselines, complex III inhibitor myxothiazol (2 µM) and adenine nucleotide translocase inhibitor carboxyatractyloside (1 µM) were added to perfusion buffer for the remainder of the imaging. Thirty minutes later, cells were treated with 100 µM levodopa and imaging continued for an additional 30 min; to test MAO inhibition, 10 µM rasagiline/5 µM clorgyline were added 30 min prior to 100 µM levodopa. Regions of interest with stable baseline fluorescence (less than 15% variation) were individually fit with centered, second order polynomial regressions (average $r^2>0.90$ in all experiments), using data from the thirty minutes following complex III/ANT inhibition (prior to levodopa administration). The mitochondrial polarization index was calculated by dividing observed data by modeled data; deviation of polarization indices from 1.0 indicated deviation from decay trajectory.

Immunohistochemistry and stereological analysis: Mice were terminally anesthetized with a mixture of ketamine (50 mg/kg)/xylazine (4.5 mg/kg) and transcardially perfused with 4% paraformaldehyde, post-fixed overnight and cryoprotected in 30% sucrose/phosphate buffered saline (PBS) at 4° C. until use. Serial coronal sections (60 µm thick) were collected throughout the midbrain and striatum. To stain for tyrosine hydroxylase the anti-tyrosine hydroxylase polyclonal antibody (Millipore) 1:2000 followed by goat anti-rabbit IgG biotin conjugated antibody (Millipore) 1:500 with normal goat serum blocking solution was used; after antibody incubation and rinsing with PBS, sections were incubated with ABC Elite Kit (Vector) and processed for diaminobenzidine reaction. Slices were mounted on slides, allowed to dry overnight, dehydrated in ascending alcohol concentrations and mounted with DPX mountant (Sigma). The estimated number of tyrosine hydroxylase positive (TH⁺) cells were stereologically counted as previously described.[27] Slices from DAT-Cre X Ai14 mice expressing TdTomato in dopaminergic neurons were mounted on slides, allowed to dry, and mounted with Prolong Gold antifade mountant (Invitrogen). The estimated number of tdTomato expressing cells were stereologically counted. Sampling for stereological quantification was done using an Olympus BX41 microscope with motorized stage (Applied Scientific Instrumentation) and computerized stereology software (Stereologer). The SNc was delineated in each animal in every other section and cells counted using a 40×/0.65NA Olympus lens.

TRAP analysis and RNA sequencing: Male hemizygous DAT bacTRAP mice[22] were randomly divided into groups of five mice. Brains were removed and sectioned using an ice-cold Adult Mouse Brain Slicer with 1 mm coronal slice intervals (Zivic Instruments). From the tissue section containing the midbrain the SNc was dissected under a Nikon SMZ645 light microscope using a 10× lens. Translated mRNAs were purified as described previously.[28] TRAP samples underwent DNase digestion using the RNase-Free DNase Set (Qiagen) and were subsequently purified with the RNeasy MinElute Cleanup Kit (Qiagen). Eluted RNA samples were analyzed on a 2100 Bioanalyzer (Agilent) using RNA Pico Chips (Agilent) to confirm RNA integrity, followed by the measurement of RNA concentrations with the Quant-iT RiboGreen RNA Assay Kit (Life Technologies). cDNAs were prepared with the Ovation RNA-Seq System V2 kit (NuGEN), using an input of 1 ng RNA. 500 ng cDNA from each sample were fragmented on a Covaris S2 Focused Ultrasonicator using the operating conditions recommended by the manufacturer for a target fragment size of 200 bp. Fragment size was confirmed on a 2100 Bioanalyzer using High Sensitivity DNA Chips (Agilent). Libraries for RNA sequencing were prepared with the TruSeq RNA Sample Preparation v2 kit (Illumina), starting the manufacturer's low-throughput protocol with the end repair step. The concentration of the RNA-Seq libraries was determined on a 2100 Bioanalyzer using High Sensitivity DNA Chips. Subsequently, two libraries with different adapters were multiplexed for sequencing. After confirming the concentration of the multiplexed samples on a 2100 Bioanalyzer using High Sensitivity DNA Chips, samples were analyzed on an Illumina HiSeq 2000 sequencer using 100 bp single-end sequencing. RNA-Seq reads were mapped to the Mus musculus assembly 10 reference genome using TopHat version 2.0.11. FPKM values for all genes in each sample were calculated with Cufflinks version 2.2.1. To analyze differential gene expression between samples, DESeq version 1.14.0 was used under the standard comparison mode.

Mass spectrometry and protein analysis: DAT-cre-Risp mice were used to perform mass spectrometry. Mice were terminally anesthetized with a mixture of ketamine (50 mg/kg)/xylazine (4.5 mg/kg) and transcardially perfused with ice cold modified artificial cerebrospinal fluid (aCSF) containing in mM: 185.0 Sucrose, 2.5 KCl, 0.5 $CaCl_2$, 10.0 $MgCl_2$, 25 $NaHCO_3$, 1.25 $NaH_2PO_4$, and 25 glucose. Once perfused the brain was rapidly removed and coronal slices containing SNc (220 µm thick) sectioned using a vibratome (VT1200S Leica Microsystems). Slices were transferred to a holding chamber containing normal aCSF in mM: 125.0 NaCl, 2.5 KCl, 2.0 $CaCl_2$, 1.0 $MgCl_2$, 25 $NaHCO_3$, 1.0 $NaH_2PO_4$, and 25 glucose and allowed 15 minutes at room temperature to recover prior to experiments. All solutions were pH 7.4, 310-320 mOsm and continually bubbled with 95% $O_2$/5% $CO_2$. From the tissue section containing the midbrain the SNc was dissected under a Nikon SMZ645 light microscope using a 10 X lens and frozen in liquid nitrogen.

Proteomics data acquisition and processing: Peptides were analyzed by LC-MS/MS using a Dionex UltiMate 3000 Rapid Separation nanoLC coupled to a linear ion trap—Orbitrap hybrid mass spectrometer (LTQ Velos Orbitrap, Thermo Fisher, San Jose, Calif., USA). Peptide samples were loaded onto the trap column, which was 150 µm×3 cm in-house packed with 3 um ReproSil-Pur® beads (Maisch, GmbH), at flow rate of 5 µL/min for 5 min using a loading buffer of acetonitrile (ACN)/H2O/formic acid (5/94.9/0.1, v/v/v). The analytical column was a 75 µm×10.5 cm PicoChip column packed with 1.9 µm ReproSil-Pur® beads (New Objectives). The flow rate was kept at 300 nL/min. For mobile phase, solvent A was 0.1% FA in water and solvent B was 0.1% FA in ACN. Peptides were separated and eluted using an acetonitrile gradient of 5-40% (mobile phase-B). The mass spectrometer was operated in data-dependent mode. The source voltage was 2.40 kV and the capillary temperature was 275° C. MS1 scans were acquired from 400-2000 m/z at 60,000 resolving power and automatic gain control (AGC) set to 1×106. The top ten most abundant precursor ions in each MS1 scan were selected for fragmentation. Precursors were selected with an isolation width of 1 Da and fragmented by collision-induced dissociation (CID) at 35% normalized collision energy in the ion trap, Previously selected ions were dynamically excluded from re-selection for 60 seconds. The MS2 AGC was set to $3\times10^5$.

Drug treatment: In vivo drug treatments included repeated saline, (+)-methamphetamine, or reserpine administration; all injections were intraperitoneal. To deplete mice of monoamines reserpine (5 mg/kg) was administered for five consecutive days and experiments performed on the fifth day of treatment;[29] mice were monitored daily and provided supplementary care as needed. To determine the effects of chronic methamphetamine mice were treated daily for 28 consecutive days with (+)-methamphetamine hydrochloride (5 mg/kg; Sigma-Aldrich) and mice sacrificed on the $28^{th}$ day. To determine whether MAO inhibition could prevent methamphetamine-induced effects, rasagiline (1 mg/kg) was administered as a 30 minute pretreatment prior to each methamphetamine injection. Drug application in ex vivo brain slice or iPSC experiments was performed via perfusion in aCSF. For ex vivo experiments all drugs were dissolved in deionized water and kept frozen as stock solutions until use with the exception of levodopa and dithiothreitol that were made fresh; aldrithiol was dissolved in pure ethanol as a stock solution and dissolved to the appropriate concentration daily.

Statistics: All data were analyzed in Prism (GraphPad Software La Jolla, Calif.) using non-parametric statistics and presented as box-and-whisker plots depicting median, quartiles, and range. Mann-Whitney (two tailed), Wilcoxon matched-pairs signed rank (two-tailed), and Kruskal-Wallis with Dunns post-hoc analyses were used where appropriate. For clarity, all data are normalized to respective controls and presented as a percent; $\alpha=0.05$.

Results

Figure 5:
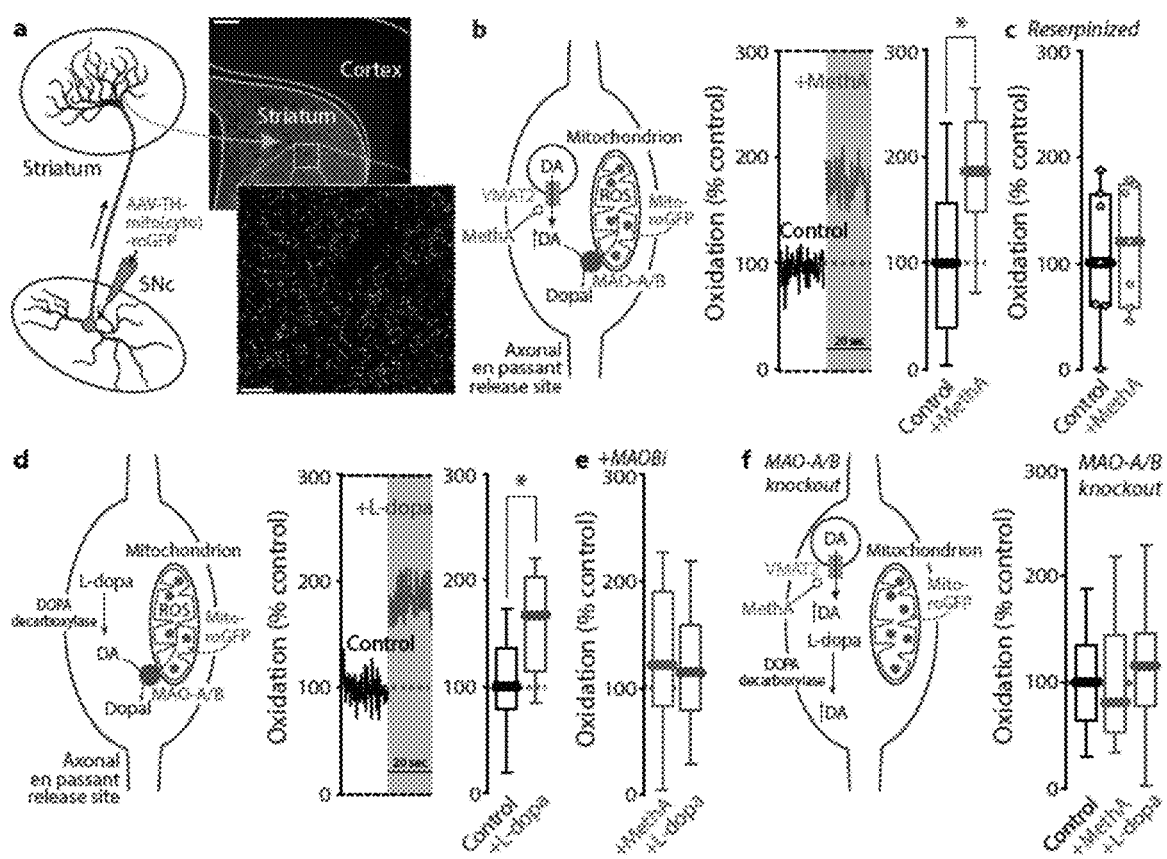
FIG. 5. Mitochondrial stress is increased by elevating cytosolic dopamine and prevented by inhibiting monoamine oxidase enzymes in ex vivo brain slices. (Panel A) Cartoon (left) depicting viral delivery of the redox sensitive probe roGFP into dopamine neurons of the substantia nigra pars compacta (SNc). The roGFP probe expresses throughout dopamine neurons as evidenced by sample images in the dorsolateral striatum (right) with roGFP (targeted to mitochondrial matrix) being expressed in dopaminergic axons. Low (upper left; scale bar denotes 500 µm) and high (lower right; scale bar denotes 10 µm) illustrating striatal expression of roGFP. (Panel B) Cartoon (left) depicting the actions of methamphetamine (methA) on vesicular monoamine transporter 2 (VMAT2) in axonal en passant release sites of dopaminergic neurons. MethA (+methA) increased mitochondrial stress in dopaminergic axons; sample traces (middle) illustrating meth-induced effects on mitochondrial stress compared to control. Perfusion of 10 µM methA (+methA; n=18 slices/9 mice) increased axonal mitochondrial stress (right) relative to control (n=19 slices/10 mice); Kruskal-Wallis test; p=0.0043). (Panel C) +methA (10 µM) had no effect on axonal mitochondrial stress in slices from reserpinized mice; n=7 slices/6 mice (Mann Whitney test; p=0.8048). (Panel D) Cartoon depicting levodopa (1-dopa) effects on cytosolic DA and mitochondrial stress in dopaminergic axonal en passant release sites (left); +1-dopa (100 µM) increased mitochondrial stress in dopaminergic axons; sample traces (middle) illustrating +1-dopa-induced effects on mitochondrial stress compared to control. Similar to +methA, +1-dopa (n=20 slices/6 mice) increased axonal mitochondrial stress (right) relative to control (n=14 slices/4 mice); Kruskal-Wallis test; p=0.0001. (Panel E) Both +methA (10 µM) and +1-dopa (100 µM)-induced axonal mitochondrial stress was prevented by 10 µM rasagaline, a monoamine oxidase B inhibitor (+MAOBi); +methA (n=18 slices/6 mice) and +1-dopa (n=20 slices/6 mice). (Panel F) Cartoon illustrating MAO-AB knockout scenario (left); neither +methA (10 µM) or +1-dopa (100 µM) had any effect on axonal mitochondrial stress in mice lacking both MAO-A and MAO-B (right); control n=13 slices/3 mice, +methA n=11 slices/3 mice, +1-dopa n=13 slices/3 mice (Kruskal-Wallis test; p=0.6718). $*p<0.05$.

In experiments conducted during development of embodiments herein, a viral vector carrying an expression construct for a cytosolic redox-sensitive variant of green fluorescent protein (cyto-roGFP) was stereotaxically injected into the SNc of mice. After infection, cyto-roGFP expression was evident throughout dopaminergic cell bodies, dendrites and axons (Ref. 7; herein incorporated by reference in its entirety). Ex vivo brain slices from these mice were prepared and two photon laser scanning microscopy was used to measure redox status of SNc dopaminergic axons, dendrites, and cell bodies. Bath application of methamphetamine (10 µM), which increases cytosolic DA by targeting vesicular monoamine transporters (VMATs) (Ref. 8, herein incorporated by reference in its entirety), failed to increase cytosolic oxidant stress in either cell bodies, dendrites or in striatal axons (FIG. 9). The DA precursor levodopa (100 µM), which also boosts cytosolic DA by increasing synthesis (Ref. 9; herein incorporated by reference in its entirety), also had no effect on cytosolic oxidant stress (FIG. 9). In contrast, bath application of 20 µM menadione robustly increased the cyto-roGFP oxidation state (>200% above baseline). Although neither methamphetamine nor levodopa affected cytosolic redox, both significantly increased mitochondrial oxidant stress selectively in axons (FIG. 5b,d) as measured with a variant of roGFP that was targeted to the mitochondrial matrix (mito-roGFP) (Ref. 10; herein incorporated by reference in its entirety). However, neither drug had any effect on somatic mitochondrial redox status (FIG. 10). Depletion of vesicular DA by pretreating mice with reserpine eliminated the mitochondrial redox effects of methamphetamine (FIG. 5c). Cocaine, which blocks the plasma membrane DA transporter but does not inhibit VMATs (Ref. 11; herein incorporated by reference in its entirety), had no effect on mitochondrial matrix redox status (FIG. 11).

Experiments were conducted during development of embodiments herein to determine whether electrons displaced by metabolism of DA are not transferred directly to $O_2$, but rather are shuttled through the intermembrane space into the electron transport chain (ETC). By that mechanism, DA metabolism by MAO would contribute to the inner membrane potential, which is used by complex V to produce ATP.

The specific type of MAO expressed by SNc dopaminergic neurons was examined. In agreement with recent work in human dopaminergic neurons (Ref. 12; herein incorporated by reference in its entirety), bacTRAP profiling of messenger ribonucleic acid (mRNA) in mouse SNc dopaminergic neurons detected both MAO-A and MAO-B variants (Table 1). When brain slices were pre-incubated with rasagiline, a selective inhibitor of MAO-B, the effects of both methamphetamine and levodopa on mitochondrial oxidant stress were attenuated (FIG. 1e; FIG. 10). Similarly, pre-incubation with the selective MAO-A inhibitor clorgyline diminished the mitochondrial redox effects of methamphetamine and levodopa (FIGS. 10, 12). Neither rasagiline nor clorgyline had any effect on basal mitochondrial oxidant stress (FIG. 13). To ensure the actions of rasagiline and clorgyline were dependent upon MAOs (Ref. 13; herein incorporated by reference in its entirety), these experiments were repeated in mice in which both MAO-A and MAO-B had been genetically deleted (Ref. 14; herein incorporated by reference in its entirety). Neither methamphetamine nor levodopa increased axonal mitochondrial oxidant stress in brain slices from these double knockout mice (FIG. 5f).

TABLE 1

Monoamine oxidase A and B mRNA are present in substantia nigra pars compacta dopaminergic neurons.

| | mean (RPKM) |
|---|---|
| Monoamine oxidase A | 19.76 |
| Monoamine oxidase B | 4.49 |

To verify that the ability of cytosolic DA to increase mitochondrial oxidant stress was not peculiar to mouse dopaminergic neurons, human dopaminergic neurons were differentiated from induced pluripotent stem cells and the experiments with levodopa repeated. Levodopa increased mitochondrial matrix oxidant stress in human dopaminergic neurons in a MAO-dependent manner, demonstrating the generality of the response (FIG. 14).

One of the limitations of the ex vivo slice preparation is that pacemaking activity generated in the somatodendritic membrane of SNc dopaminergic neurons is not propagated to axon terminals. This spike activity and the metabolic demands it poses could increase the sensitivity of axonal mitochondria to MAO metabolism by elevating basal oxidative phosphorylation. The extracellular $K^+$ concentration was increased to 15 mM to modestly depolarize axons (Ref. 15; herein incorporated by reference in its entirety). This change had no discernible effect on mitochondrial oxidant stress. By contrast, a stronger depolarizing stimulus achieved by a higher concentration of $K^+$ (30 mM) or opening of Cav1 $Ca^{2+}$ channels with the potentiator Bay K 8644 increased mitochondrial stress (FIG. 16). However, when the modest (15 mM) depolarization was paired with a low dose of methamphetamine (1 µM), which also on its own had no measurable effect on mitochondrial redox status, there was a significant elevation in mitochondrial oxidant stress (FIG. 8c).

Figure 6:
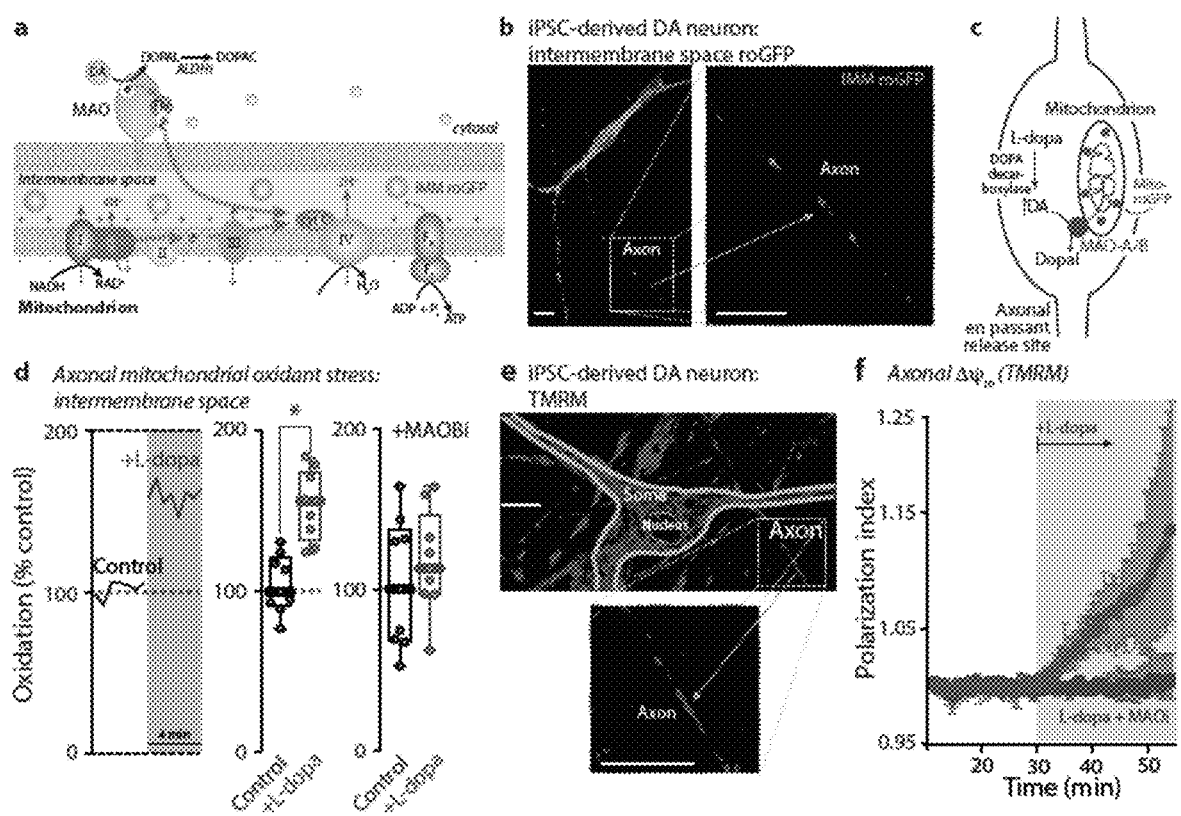
FIG. 6. Elevating cytosolic dopamine with levodopa increased mitochondrial stress by transferring electrons to the intermembrane space in human iPSC-derived dopamine neurons. (Panel A) Cartoon depicting the transfer of electrons from monoamine oxidase (MAO) metabolism of dopamine (DA) to mitochondrial intermembrane space. (Panel B) An image of an iPSC expressing the redox sensitive probe roGFP in the mitochondrial intermembrane space (left) and high magnification highlighting an axonal segment (right); scale bars denote 10 µm. (Panel C) Cartoon depicting effect of levodopa (1-dopa) and the selective expression of the mito-roGFP probe in the intermembrane space. (Panel D) Sample traces (left) illustrating 100 µM levodopa (+1-dopa)-induced increase in intermembrane stress relative to control.

For electrons generated by MAO metabolism of DA to reach the ETC, they would have to traverse the intermembrane space. This is plausible given that MAO binds flavin adenine dinucleotide (FAD), which can act as an electron shuttle, and many of the proteins that reside within the intermembrane space are capable of shuttling electrons (Ref. 16; herein incorporated by reference in its entirety) (FIG. 6a). In experiments conducted during development of embodiments herein to determine whether MAO activity increases the flux of electrons through the intermembrane space, a roGFP expression construct with an intermembrane space targeting sequence (Ref. 17; herein incorporated by reference in its entirety) was introduced into human dopaminergic neurons; after allowing expression of the protein (FIG. 6b), neurons were exposed to levodopa. Levodopa robustly increased oxidant stress within the intermembrane space and this stress was attenuated by MAO inhibition (FIG. 6d).

There results are consistent with the existence of a shuttle or that local production of hydrogen peroxide was responsible for the IMS roGFP signal. If MAO-derived electrons are shuttled to cytochrome c and complex IV, then MAO activity would increase proton pumping by complex IV and increase the inner mitochondrial membrane (IMM) potential, whereas local production of hydrogen peroxide would not have that effect. The cationic dye tetramethylrhodamine (TMRM) was used to monitor IMM potential (ref. 10; herein incorporated by reference in its entirety) (FIG. 6e). To isolate complex IV, complex III was inhibited with 1 myxothiazol (1 µM) to block electron flux from earlier complexes in the ETC, and the adenine nucleotide translocase (ANT) was inhibited with 1 µM carboxyatractyloside (1 µM) to prevent cytosolic ATP from entering the mitochondria and driving complex V in reverse. Inhibition of complex III and ANT caused TMRM fluorescence to fall. The trajectory of the fall was fit mathematically (FIG. 15). In agreement with the proposition that MAO metabolism of DA was increasing complex IV activity, bath application of levodopa consistently slowed the decline in TMRM fluorescence (FIG. 6f). Given that cytochrome c is the proximal carrier of electrons into complex IV, these data indicate that electrons derived from MAO activity are transferred through the intermembrane space to cytochrome c, and subsequently to cytochrome c oxidase. Genetic deletion of an essential subunit of complex III (Rieske iron-sulfur protein, Uqcrfs1) in SNc dopaminergic neurons induced a dramatic up-regulation in MAO-B expression (FIG. 17), indicating that the MAO shuttle could compensate for a complex III deficit.

These data indicate that in both mouse and human dopaminergic neurons, MAO oxidative deamination of DA results in the shuttling of electrons through the mitochondrial intermembrane space to the ETC (FIG. 6a), contributing to polarization of the inner mitochondrial membrane and thus the generation of ATP. In that regard, activity-dependent recycling of DA through the cytosol at axonal release sites allows MAO to play a salutory role in helping the mitochondria meet the bioenergetic demands associated neurotransmission. But, as with other factors that increase the inner mitochondrial membrane potential, this comes at the expense of increased mitochondrial oxidant stress.

A sustained increase in mitochondrial oxidant stress has been hypothesized to underlie the selective vulnerability of SNc dopaminergic neurons in PD (Ref. 18; herein incorporated by reference in its entirety). In healthy SNc dopaminergic neurons, mitochondrial oxidant stress is elevated relative to ventral tegmental area (VTA) dopaminergic neurons in both axonal and somatodendritic compartments (Refs. 10, 19; herein incorporated by reference in their entireties). But this stress is not sufficient to produce a significant level of neurodegeneration in mouse models. Nevertheless, in this cellular context, methamphetamine-driven MAO activity could create a 'second hit' for mitochondria, increasing oxidant stress levels to a point where normal quality control mechanisms fail, irreversible damage is done and neurodegeneration is triggered. Mice were administered a modest dose of methamphetamine (5 mg/kg, ip) for 28 consecutive days. This regimen significantly decreased tyrosine hydroxylase (TH) immunoreactivity in the SNc (FIG. 7a). To distinguish between phenotypic down-regulation and frank neurodegeneration, experiments were repeated with mice in which SNc dopaminergic neurons expressed tdTomato under the control of a constitutive promoter (FIG. 7b, c). Again, methamphetamine treatment led to a loss of tdTomato fluorescence in both the striatum and SNc neurons, indicating that there was frank degeneration (FIG. 7b). Critically, administration of the MAO-B inhibitor rasagiline prior to starting methamphetamine treatment significantly reduced degeneration in both the striatum and SNc (FIG. 7a-c).

Experiments conducted during development of embodiments herein provide a mechanistic explanation for the epidemiological association between methamphetamine abuse and increased risk of PD (refs. 1-3; herein incorporated by reference in their entireties).

In addition to methamphetamine (e.g. Desoxyn), amphetamine formulations (e.g., Adderall and Adderall XR) are commonly used to treat ADHD.[20] Like methamphetamine, amphetamine increases cytosolic DA (Ref. 8; herein incorporated by reference in its entirety). Indeed, d-amphetamine increased mitochondrial oxidant stress in SNc DA axons in a MAO-dependent manner, as did methamphetamine (FIG. 8a). In contrast, methyphenidate (Ritalin), which does not directly target vesicular transporters, had no effect on mitochondrial oxidant stress (FIG. 8b).

Collectively, Experiments conducted during development of embodiments herein demonstrate that in addition to limiting the accumulation of cytosolic DA, mitochondrially anchored MAO helps to meet the bioenergetic needs of neurotransmission by promoting mitochondrial oxidative phosphorylation. While beneficial under normal circumstances, excessive stimulation of MAO by drugs that release vesicular DA (methamphetamine and amphetamine) or increase DA synthesis (levodopa) dramatically increases mitochondrial oxidant stress and trigger degeneration of SNc dopaminergic neurons. These results not only provide a mechanistic foundation for the epidemiological linkage between methamphetamine abuse and PD, but also raise a cautionary flag about the clinically sanctioned use of methamphetamine or amphetamine for the treatment of other conditions, including ADHD, obesity and narcolepsy (Ref. 21; herein incorporated by reference in its entirety). These data indicate that sustained use of amphetamines from adolescence into adulthood accelerates the loss of SNc dopaminergic neurons and increases the likelihood of developing PD. Moreover, they indicate that the neuropathological liability of the amphetamines (e.g., in those cases where alternatives, like methylphenidate (Ritalin), are not clinically viable) is mitigated by co-administration of a well-tolerated MAO-B inhibitor.

REFERENCES

The following references, some of which are cited above by number, are herein incorporated by reference in their entireties.

1 Callaghan, R. C., Cunningham, J. K., Sajeev, G. & Kish, S. J. Incidence of Parkinson's disease among hospital patients with methamphetamine-use disorders. Mov Disord 25, 2333-2339, doi:10.1002/mds.23263 (2010).

2 Callaghan, R. C., Cunningham, J. K., Sykes, J. & Kish, S. J. Increased risk of Parkinson's disease in individuals hospitalized with conditions related to the use of methamphetamine or other amphetamine-type drugs. Drug Alcohol Depend 120, 35-40, doi:10.1016/j.drugalcdep.2011.06.013 (2012).

3 Curtin, K. et al. Methamphetamine/amphetamine abuse and risk of Parkinson's disease in Utah: a population-based assessment. Drug Alcohol Depend 146, 30-38, doi:10.1016/j.drugalcdep.2014.10.027 (2015).

4 Segura-Aguilar, J. et al. Protective and toxic roles of dopamine in Parkinson's disease. J Neurochem 129, 898-915, doi:10.1111/jnc.12686 (2014).

5 Fahn, S. & Cohen, G. The oxidant stress hypothesis in Parkinson's disease: evidence supporting it. Ann Neurol 32, 804-812, doi:10.1002/ana.410320616 (1992).

6 Kaludercic, N., Deshwal, S. & Di Lisa, F. Reactive oxygen species and redox compartmentalization. Front Physiol 5, 285, doi:10.3389/fphys.2014.00285 (2014).

7 Dryanovski, D. I. et al. Calcium entry and alpha-synuclein inclusions elevate dendritic mitochondrial oxidant stress in dopaminergic neurons. J Neurosci 33, 10154-10164, doi:10.1523/JNEUROSCI.5311-12.2013 (2013).

8 Sulzer, D., Sonders, M. S., Poulsen, N. W. & Galli, A. Mechanisms of neurotransmitter release by amphetamines: a review. Prog Neurobiol 75, 406-433, doi:10.1016/j.pneurobio.2005.04.003 (2005).

9 Mosharov, E. V. et al. Interplay between cytosolic dopamine, calcium, and alpha-synuclein causes selective death of substantia nigra neurons. Neuron 62, 218-229, doi:10.1016/j.neuron.2009.01.033 (2009).

10 Guzman, J. N. et al. Oxidant stress evoked by pacemaking in dopaminergic neurons is attenuated by DJ-1. Nature 468, 696-700, doi:10.1038/nature09536 (2010).

11 Pifl, C., Drobny, H., Reither, H., Hornykiewicz, O. & Singer, E. A. Mechanism of the dopamine-releasing actions of amphetamine and cocaine: plasmalemmal dopamine transporter versus vesicular monoamine transporter. Mol Pharmacol 47, 368-373 (1995).

12 Woodard, C. M. et al. iPSC-derived dopamine neurons reveal differences between monozygotic twins discordant for Parkinson's disease. Cell Rep 9, 1173-1182, doi:10.1016/j.celrep.2014.10.023 (2014).

13 Lamensdorf, I., Youdim, M. B. & Finberg, J. P. Effect of long-term treatment with selective monoamine oxidase A and B inhibitors on dopamine release from rat striatum in vivo. J Neurochem 67, 1532-1539 (1996).

14 Chen, K., Holschneider, D. P., Wu, W., Rebrin, I. & Shih, J. C. A spontaneous point mutation produces monoamine oxidase AB knock-out mice with greatly elevated monoamines and anxiety-like behavior. J Biol Chem 279, 39645-39652, doi:10.1074/jbc.M405550200 (2004).

15 Hille, B. Ion channels of excitable membranes. 3rd edn, (Sinauer, 2001). Brand, M. D. Mitochondrial generation of superoxide and hydrogen peroxide as the source of mitochondrial redox signaling. Free Radic Biol Med 100, 14-31, doi:10.1016/j.freeradbiomed.2016.04.001 (2016).

17 Sabharwal, S. S., Waypa, G. B., Marks, J. D. & Schumacker, P. T. Peroxiredoxin-5 targeted to the mitochondrial intermembrane space attenuates hypoxia-induced reactive oxygen species signalling. Biochem J 456, 337-346, doi:10.1042/BJ20130740 (2013).

18 Surmeier, D. J. & Schumacker, P. T. Calcium, bioenergetics, and neuronal vulnerability in Parkinson's disease. J Biol Chem 288, 10736-10741, doi:10.1074/jbc.R112.410530 (2013).

19 Pacelli, C. et al. Elevated Mitochondrial Bioenergetics and Axonal Arborization Size Are Key Contributors to the Vulnerability of Dopamine Neurons. Curr Biol 25, 2349-2360, doi:10.1016/j.cub.2015.07.050 (2015).

20 Hodgkins, P., Shaw, M., McCarthy, S. & Sallee, F. R. The pharmacology and clinical outcomes of amphetamines to treat ADHD: does composition matter? CNS Drugs 26, 245-268, doi:10.2165/11599630-000000000-00000 (2012).

21 Christine, C. W., Marks, W. J., Jr. & Ostrem, J. L. Development of Parkinson's disease in patients with Narcolepsy. J Neural Transm (Vienna) 119, 697-699, doi:10.1007/s00702-011-0761-z (2012).

22 Brichta, L. et al. Identification of neurodegenerative factors using translatome-regulatory network analysis. Nat Neurosci 18, 1325-1333, doi:10.1038/nn.4070 (2015).

23 Seibler, P. et al. Mitochondrial Parkin recruitment is impaired in neurons derived from mutant PINK1 induced pluripotent stem cells. J Neurosci 31, 5970-5976, doi:10.1523/JNEUROSCI.4441-10.2011 (2011).

24 Mazzulli, J. R. et al. Gaucher disease glucocerebrosidase and alpha-synuclein form a bidirectional pathogenic loop in synucleinopathies. Cell 146, 37-52, doi:10.1016/j.cell.2011.06.001 (2011).

25 Cooper, O. et al. Pharmacological rescue of mitochondrial deficits in iPSC-derived neural cells from patients with familial Parkinson's disease. Sci Transl Med 4, 141ra190, doi:10.1126/scitranslmed.3003985 (2012).

26 Kriks, S. et al. Dopamine neurons derived from human ES cells efficiently engraft in animal models of Parkinson's disease. Nature 480, 547-551, doi:10.1038/nature10648 (2011).

27 Ilijic, E., Guzman, J. N. & Surmeier, D. J. The L-type channel antagonist isradipine is neuroprotective in a mouse model of Parkinson's disease. Neurobiol Dis 43, 364-371, doi:10.1016/j.nbd.2011.04.007 (2011).

28 Heiman, M., Kulicke, R., Fenster, R. J., Greengard, P. & Heintz, N. Cell type-specific mRNA purification by translating ribosome affinity purification (TRAP). Nat Protoc 9, 1282-1291, doi:10.1038/nprot.2014.085 (2014).

29 Day, M. et al. Selective elimination of glutamatergic synapses on striatopallidal neurons in Parkinson disease models. Nat Neurosci 9, 251-259, doi:10.1038/nn1632 (2006).

The invention claimed is:

1. A method comprising co-administering (i) a monoamine oxidase (MAO) inhibitor and (ii) amphetamine and/or methamphetamine to a subject suffering from attention deficit hyperactive disorder (ADHD), narcolepsy, or obesity.

2. The method of claim 1, wherein the monoamine oxidase inhibitor is a nonselective MAO-A/MAO-B inhibitor.

3. The method of claim 2, wherein the nonselective MAO-A/MAO-B inhibitor is selected from the group consisting of isocarboxazid, nialamide, phenelzine, hydracarbazine, and tranylcypromine.

4. The method of claim 1, wherein the monoamine oxidase inhibitor is an MAO-A inhibitor.

5. The method of claim 4, wherein the MAO-A inhibitor is selected from the group consisting of bifemelane, moclobemide, pirlindole, toloxatone.

6. The method of claim 1, wherein the monoamine oxidase inhibitor is an MAO-B inhibitor.

7. The method of claim 6, wherein the MAO-B inhibitor is selected from the group consisting of selegiline and rasagiline.

8. The method of claim 1, wherein the MAO inhibitor, amphetamine and/or methamphetamine are administered concurrently.

9. The method of claim 1, wherein the MAO inhibitor, amphetamine and/or methamphetamine are administered separately.

* * * * *